US011994451B2

(12) United States Patent
Hurtado

(10) Patent No.: US 11,994,451 B2
(45) Date of Patent: May 28, 2024

(54) OPTICAL CLEARING AND AUTO-FLUORESCENCE QUENCHING SOLUTIONS AND METHOD OF USE FOR ENHANCED MICROSCOPY IMAGING OF BIOLOGICAL TISSUES

(71) Applicant: CORNELL UNIVERSITY, Ithaca, NY (US)

(72) Inventor: Romulo Hurtado, Ithaca, NY (US)

(73) Assignee: CORNELL UNIVERSITY, Ithaca, NY (US)

(*) Notice: Subject to any disclaimer, the term of this patent is extended or adjusted under 35 U.S.C. 154(b) by 439 days.

(21) Appl. No.: 17/294,504

(22) PCT Filed: Nov. 20, 2019

(86) PCT No.: PCT/US2019/062321
§ 371 (c)(1),
(2) Date: May 17, 2021

(87) PCT Pub. No.: WO2020/106788
PCT Pub. Date: May 28, 2020

(65) Prior Publication Data
US 2021/0404918 A1    Dec. 30, 2021

Related U.S. Application Data

(60) Provisional application No. 62/770,208, filed on Nov. 21, 2018.

(51) Int. Cl.
*G01N 1/30* (2006.01)
*G01N 21/64* (2006.01)
*G01N 33/50* (2006.01)

(52) U.S. Cl.
CPC ........... *G01N 1/30* (2013.01); *G01N 21/6428* (2013.01); *G01N 21/6458* (2013.01);
(Continued)

(58) Field of Classification Search
CPC .. G01N 1/30; G01N 21/6428; G01N 21/6458; G01N 33/5058; G01N 33/5061;
(Continued)

(56) References Cited

U.S. PATENT DOCUMENTS 6,232,092 B1    5/2001 Rogers
6,472,216 B1 *  10/2002 Chiang .................... G01N 1/30
                                          435/40.51
(Continued)

FOREIGN PATENT DOCUMENTS

CN    106568753 A  *  4/2017
CN    108106909 A     6/2018
(Continued)

OTHER PUBLICATIONS

Azaripour, A., et al., "A survey of clearing techniques for 3D imaging of tissues with special reference to connective tissue", Progress in Histochemistry and Cytochemistry (2016), Accepted Apr. 11, 2016, pp. 9-23, 51.
(Continued)

*Primary Examiner* — Marcos L Torres
(74) *Attorney, Agent, or Firm* — Scully, Scott, Murphy & Presser, P.C.

(57) ABSTRACT

A method for rendering biological tissue sufficiently optically transparent for three-dimensional light microscopy imaging, comprising incubating biological tissue with an optical clearing solution, wherein the optical clearing solution comprises: (i) 20-50 wt % formamide, (ii) 10-90 wt % glycerol, and (iii) water as remainder. Also described herein is a method for ridding tissue of blood to make them amenable for optical clearing, comprising incubating biological tissue in a decolorizing solution, wherein the decolorizing solution comprises: (i) 0.5-3 wt % hydrogen peroxide, (ii) 0.05-1 wt % sodium azide, (iii) 5-20 wt % DMSO,
(Continued)

and (iv) phosphate buffered saline as a remained. Also described herein is a method for reducing auto-fluorescence in biological tissue to permit imaging of the biological tissue in a fluorescence-based imaging technique with enhanced resolution, wherein the auto-fluorescence quenching solution comprises: 1-100 mM ammonium bicarbonate, (ii) 20-500 M copper sulfate, (iii) 5-20 wt % DMSO, and (iv) water as remainder.

**10 Claims, 20 Drawing Sheets
(20 of 20 Drawing Sheet(s) Filed in Color)**

(52) U.S. Cl.
CPC ..... *G01N 33/5058* (2013.01); *G01N 33/5061* (2013.01); *G01N 2021/6432* (2013.01)

(58) Field of Classification Search
CPC ....... G01N 2021/6432; G01N 21/6486; G02B 21/0076; G02B 21/16
See application file for complete search history.

(56) References Cited

U.S. PATENT DOCUMENTS

| | | |
|---|---|---|
| 2006/0039859 A1 | 2/2006 | Sharma et al. |
| 2018/0021285 A1 | 1/2018 | Crider et al. |
| 2018/0120231 A1 | 5/2018 | Wainwright et al. |
| 2019/0128785 A1* | 5/2019 | Zhao ................ G01N 1/30 |
| 2019/0187056 A1 | 6/2019 | Wainwright et al. |

FOREIGN PATENT DOCUMENTS

| | | | |
|---|---|---|---|
| WO | WO-2016023009 A1 * | 2/2016 | ............... G01N 1/30 |
| WO | 2018/113723 A1 | 6/2018 | |
| WO | 2018/155587 A1 | 8/2018 | |
| WO | 2018/224289 A1 | 12/2018 | |
| WO | 2020/106788 A1 | 5/2020 | |

OTHER PUBLICATIONS

Borlinghaus, R.T., et al., "Clearing Procedures for Deep Tissue Imaging", Imaging and Mircoscopy, Mar. 2014, pp. 14-15, vol. 16.

Cano-Raya, C., et al., "Fluorescence Quenching of the Europium Tetracycline Hydrogen Peroxide Complex by Copper (II) and Other Metal Ions", Applied Spectroscopy, Nov. 10, 2005, pp. 1209-1216, vol. 59.

Erben, T., et al., "What to do with high autofluorescence background in pancreatic tissues—an efficient Sudan black B quenching method for specific immunofluorescence labelling", First published Jan. 23, 2016, Histopathology, pp. 406-422, vol. 69, Issue 3, https://onlinelibrary.wiley.com/doi/epdf/10.1111/his.12935, Abstract only.

International Search Report and Written Opinion dated Mar. 18, 2020 issued in PCT/US 19/62321, 14 pages.

King, R.S., et al., "In situ hybridization protocol for enhanced detection of gene expression in the planarian Schmidtea mediterranea", BioMed Central Developmental Biology 2013, pp. 1-16, 13:8.

Miyawaki, A., "Optical Clearing of Biological Tissue", https://www.labome.com/method/Optical-Clearing-of-Biological-Tissue-with-ScaleA2.html, Original version Sep. 27, 2011, Last modified Oct. 27, 2020, 6 pages.

Schnell, S.A., et al., et al., "Reduction of Lipofuscin-like Autofluorescence in Fluorescently Labeled Tissue", The Journal of Histochemistry & Cytochemistry, 1999, pp. 719-730, vol. 47(6).

Silvestri, L., et al., "Clearing of fixed tissue: a review from a microscopist's perspective", Journal of Biomedical Optics, Aug. 2016, pp. 081205-1-081205-8, vol. 21(8).

* cited by examiner

OPTICAL CLEARING AND AUTO-FLUORESCENCE QUENCHING SOLUTIONS AND METHOD OF USE FOR ENHANCED MICROSCOPY IMAGING OF BIOLOGICAL TISSUES

CROSS REFERENCE TO RELATED APPLICATIONS

This application claims the benefit of priority from U.S. Provisional Application No. 62/770,208, filed on Nov. 21, 2018, which is herein incorporated by reference in its entirety.

GOVERNMENT SUPPORT

This invention was made with government support under grant number NIH R21DK116171 awarded by the National Institutes of Health. The government has certain rights in the invention.

FIELD OF THE INVENTION

The present invention generally relates to optical clearing solutions and their use in rendering biologically tissues substantially optically transparent or solutions to reduce tissue auto-fluorescence. In one aspect, the present invention more specifically relates to optical clearing solutions containing formamide and/or glycerol. In another aspect, the present invention relates to solutions to decolorize, or remove blood from tissue to make them more amenable to optical clearing, and which contains hydrogen peroxide, sodium azide, and dimethyl sulfoxide (DMSO). In another aspect, the present invention relates to solutions that function to reduce auto-fluorescence and which contain ammonium bicarbonate, DMSO, and copper sulfate.

BACKGROUND OF THE INVENTION

Visualizing cellular structures in the global context of intact organs is critical for deciphering organ function. Imaging intact organs, however, is limited in large part by two challenges: a) biological tissues are not transparent and scatter light, thus limiting the depth of imaging using light microscopy techniques; and b) biological tissues are naturally auto-fluorescent, thus making it hard to resolve the difference between background noise and signal using fluorescent light-based techniques, such as immunofluorescence (IF). Significantly, fluorescent light principles are incorporated into some of the most advanced imaging modalities used today, including confocal, super-resolution, two-photon, and light sheet microscopy.

Optical clearing methods generally include the immersion of tissues in a solution that has a refractive index (RI) that closely matches that of biological tissues, which is approximately RI=1.5. It is the immersion of tissues in a refractive-index-specified solution that makes tissues transparent. By matching the refractive index of the tissue, light is no longer scattered, and the tissue becomes optically transparent. Recent years has seen the development of several optical clearing solutions, but these techniques have a number of limitations (Yu, T. et al., *J Biophotonics* 11, doi:10.1002/jbio.201700187, 2018). Some of these limitations include, for example, technically challenging to use, a resulting increase in auto-fluorescence, high toxicity, denaturing of tissue by presence of alcohols or urea, and damage (loss of integrity) of the tissue.

SUMMARY OF THE INVENTION

The present invention overcomes persistent problems encountered in the art of imaging biological tissues, particularly solid tissues, such as connective (e.g., organ), muscular, nervous, or epithelial tissue, including whole organs. The present invention achieves this improvement by treating biological tissue with a specially formulated optical clearing solution that is easy to use, easy to make, is non-toxic, and retains structural integrity of the biological tissue. The specially formulated clearing solution provides an improved method for rendering biological tissue substantially transparent in preparation for imaging by three-dimensional light microscopy, including fluorescent light microscopy imaging. The optical clearing solution contains: (i) formamide in an amount of 20-50 wt %, (ii) glycerol in an amount of 10-90 wt %, and (iii) optionally, water as remainder. The invention achieves optical clearing of biological tissue by incubating the biological tissue with the foregoing optical clearing solution for sufficient time for the optical clearing solution to impregnate the biological tissue.

The above-described optical clearing solution overcomes a number of deficiencies encountered in current methods. Some of the advantages provided by the above optical clearing solution include: 1) capability of clearing tough, fibrous whole muscle organs, such as the heart and intestines; 2) does not require machinery; 3) does not require toxic solvents that are dangerous to users and can damage microscopes; 4) does not require dehydrating of tissues with primary alcohols, which causes loss of scarce cellular structures, such as plasma membrane proteins; 5) substantially preserves tissue integrity, including fluorescent reporter proteins; 6) does not increase sample auto-fluorescence, thereby facilitating multi-labeling fluorescent light imaging; and 7) is compatible with in vivo tracers, such as injectable fluorescent lectins. Moreover, the optical clearing solution described herein is easy to use, easy to make, is non-toxic, and retains the structural integrity of biological tissues. As noted above, the optical clearing solution described herein contains formamide and glycerol. Formamide has an RI of 1.45, which closely matches the RI of biological tissues. The use of glycerol is also advantageous because it has an RI of 1.47, it is hydrophilic and does not require tissue dehydration, which can compromise the structural integrity of samples, and it is non-toxic and user friendly.

In another aspect, the present invention provides an improved method to decolorize or rid tissue of blood, which blocks light and impedes optical clearing. The present invention achieves this by incubating the biological tissue with a decolorizing solution for sufficient time for the decolorizing solution to impregnate the biological tissue and rid the tissue of enough blood to make the tissue amenable for subsequent optical clearing. The decolorizing solution contains precisely or at least the following components: (i) hydrogen peroxide, (ii) sodium azide, (iii) DMSO, and (iv) phosphate buffered saline (PBS) as a remainder. As discussed later on in this disclosure, the above-described decolorizing solution is particularly advantageous in its ability to reduce or moderate the level of oxygen generation in biological tissue, which in turn maintains tissue integrity substantially better than peroxide-containing decolorizing solutions of the art.

In another aspect, the present invention provides an improved method for reducing auto-fluorescence in biological tissue to render the biological tissue imagable with enhanced resolution in fluorescence-based imaging techniques. The present invention achieves this by incubating the biological tissue with an auto-fluorescence quenching solution for sufficient time for the auto-fluorescence quenching solution to impregnate the biological tissue and make the biological tissue sufficiently reduced in auto-fluorescence to permit imaging of the biological tissue in a fluorescence-based imaging technique with enhanced resolution. The auto-fluorescence quenching solution contains precisely or at least the following components: (i) ammonium bicarbonate in a concentration of 1-100 mM, (ii) copper sulfate in a concentration of 100-500 µM, (iii) 5-20 wt % DMSO, and (iv) water as remainder.

The above-described auto-fluorescence quenching solution advantageously reduces auto-fluorescence in tissues being optical cleared and imaged by conventional fluorescent imaging techniques. Conventional optical clearing protocols have generally not addressed tissue auto-fluorescence, even though auto-fluorescence substantially limits imaging of intact tissues in 3D fluorescent light-based microscopy. Notably, copper ions have been reported to have auto-fluorescent quenching properties, albeit at high concentrations (millimolar range) in the presence of acidic ammonium acetate (pH=5.0), which damages proteins and fluorophores used in IF (Schnell, S. A. et al., *J. Histochem Cytochem* 47, doi: 10.1177/002215549904700601, 1999; and Yang, J. et al., *Wellcome Open Research* 2, doi: 10.12688/wellcomeopenres.12251.1, 2017). The present auto-fluorescence quenching solution utilizes ammonium bicarbonate, DMSO, and copper metal ions in water. Strikingly, the auto-fluorescent quenching solution described herein eliminates tissue auto-fluorescence using a micromolar concentration of copper ions, conserves tissue protein expression, and by consequence, dramatically increases the signal-to-noise ratio of IF studies.

BRIEF DESCRIPTION OF THE FIGURES

The patent or application file contains at least one drawing executed in color. Copies of this paper or patent application publication with color drawing(s) will be provided by the Office upon request and payment of the necessary fee.

FIG. 1A shows a series of micrographs of tissue sections of varied thickness (i.e., 100, 250, and 500 µm), each treated with either PBS, ClearT$^2$ (conventional clearing solution containing 50% formamide and 20% PEG), or Atacama Clear (i.e., AT-C, of the present invention). FIG. 1B is a graph plotting the quantified visibility (i.e., grid visibility ratio) of the grid paper below the tissue being imaged for tissue treated with PBS, ClearT$^2$ (of the art), and Atacama Clear (of the present invention) for the same 100, 250, and 500 µm thickness samples shown in FIG. 1A. Notably, Atacama Clear exhibits 50% greater efficacy in optically clearing muscle.

FIG. 2A shows micrographs of heart muscle tissue treated with a standard peroxide decolorizing solution (top frame) or alternatively treated with Atacama-$H_2O_2$ (bottom frame). Atacama-$H_2O_2$ prevents the generation of abundant oxygen pockets inside samples (arrows in standard $H_2O_2$ micrograph point to oxygenation, which is precluded in Atacama-$H_2O_2$). FIG. 2B shows micrographs of the heart muscle tissue treated with either standard peroxide decolorizing solution (left column) or Atacama-$H_2O_2$ (right column) In standard $H_2O_2$ treatments, the abundant oxygenation results in tissue tearing (black arrows in high magnification panel). This tissue tearing is precluded in Atacama-$H_2O_2$ (high magnification panel). FIG. 2C shows micrographs of heart muscle tissue of 1 mm thickness (i) before any treatment (left frame), (ii) treated with Atacama-$H_2O_2$ (middle frame), and (iii) subsequently treated with Atacama Clear subsequent to Atacama-$H_2O_2$ treatment (right frame).

FIG. 9A shows the level of AF in images of untreated (top) and AQ-treated (bottom) human brain tissue. The level of AF observed in these tissues is quantified in graphs shown in FIG. 9B.

FIG. 10 (top panel) shows a micrograph of untreated tissue from an animal expressing Venus fluorescent protein in interstitial cells. As can be seen in this top panel of non-treated tissue, Venus$^+$ cells could be detected (non-treated, white arrow), although background green fluorescence (non-treated, white star) made it difficult to distinguish Venus$^+$ cells from background in certain regions (non-treated, red arrow). FIG. 10 (bottom panel) shows a micrograph of tissue from the animal expressing Venus fluorescent protein in interstitial cells, treated with Atacama Quench (AQ treatment). By contrast to untreated tissue, tissues treated with Atacama Quench exhibited a uniform Venus$^+$ signal, and lacked background auto-fluorescence.

DETAILED DESCRIPTION OF THE INVENTION

Figure 1A:
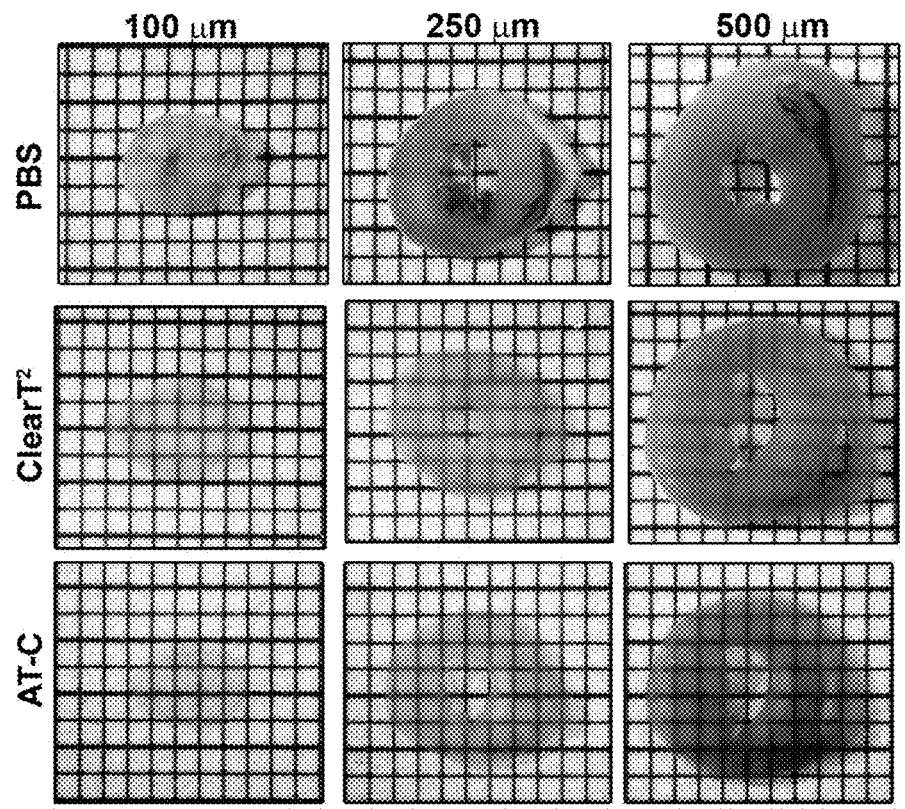
FIGS. 1A-1B.

In one aspect, the present disclosure is directed to a method for rendering biological tissue sufficiently optically transparent for three-dimensional light microscopy imaging. In the method, biological tissue is incubated with an optical clearing solution for sufficient time for the optical clearing solution to impregnate the biological tissue and make the biological tissue sufficiently optically transparent for three-dimensional light microscopy imaging, such as fluorescent microscopy imaging. As well known in the art, the term "sufficient time," in reference to the time of incubation, can be varied depending on how thick and tough the tissue is, and whether the tissue is embryonic or adult. Smaller and less tough tissues, as well as embryonic tissues require less incubation. As well known in the art, the term "sufficiently optically transparent" refers to a level of transparency that permits an adequate level of imaging and adequate discernment of fine structural details of the tissue.

The optical clearing solution typically includes at least the following three components: (i) formamide (methanamide) in an amount of 20-50 wt %, (ii) glycerol in an amount of 10-90 wt %, and (iii) water as remainder. In some embodiments, the optical clearing solution contains only the foregoing three components. In other embodiments, the optical solution includes one or more additional components (e.g., PEG, PBS, boric acid, sodium azide, or ammonium bicarbonate), typically in an amount of no more than or less than 10 wt %, more typically no more than or less than 5 wt %, 2 wt %, or 1 wt %. In some embodiments, alcohols and/or ethers are excluded from the clearing solution. In different embodiments, the formamide is present in the clearing solution in an amount of, for example, 20, 25, 30, 35, 40, 45, or 50 wt %, or an amount within a range bounded by any two of the foregoing values (e.g., 20-45 wt %, 20-40 wt %, 20-35 wt %, 20-30 wt %, 25-45 wt %, 25-40 wt %, 25-35 wt %, or 25-30 wt %). In different embodiments, the glycerol is present in the clearing solution in an amount of, for example, 10, 15, 20, 25, 30, 35, 40, 45, 50, 55, 60, 65, 70, 75, 80, 85, or 90 wt %, or an amount within a range bounded by any two of the foregoing values (e.g., 30-90 wt %, 35-90 wt %, 40-90 wt %, 45-90 wt %, 50-90 wt %, 55-90 wt %, 60-90 wt %, 30-80 wt %, 35-80 wt %, 40-80 wt %, 45-80 wt %, 50-80 wt %, 55-80 wt %, or 60-80 wt %). In some embodiments, the clearing solution contains more glycerol than formamide, while in other in other embodiments, the clearing solution contains more formamide than glycerol. In some embodiments, the total of formamide and glycerol represents at least or more than 40 wt %, 50 wt %, 55 wt %, 60 wt %, 65 wt %, 70 wt %, 75 wt %, or 80 wt % of the clearing solution. Although water is typically present in the clearing solution, the possibility remains that water may be present in a minute amount (e.g., no more than or less than 5 wt %, 4 wt %, 3 wt %, or 2 wt %) or substantially absent (typically no more than or less than 1, 0.5, or 0.1 wt %, or 0 wt %). In the case of water being completely or substantially absent, the formamide and glycerol may be selected to be in amounts that sum to 100 wt % (e.g., 10 wt % formamide and 90 wt % glycerol, 20 wt % formamide and 80 wt % glycerol, or 30 wt % formamide and 70 wt % glycerol, or 40 wt % formamide and 60 wt % glycerol, or 50 wt % formamide and 50 wt % glycerol).

To render the biological tissue sufficiently optically transparent for three-dimensional light microscopy, the biological tissue is incubated with the optical clearing solution described above for sufficient time for the optical clearing solution to fully impregnate the biological tissue. As indicated above, the incubation time can be varied depending on how thick and tough the tissue is, and whether the tissue is embryonic or adult. Smaller and less tough tissues, as well as embryonic tissues require less incubation. Depending on the above and other factors, the tissue may be incubated for a time of, for example, 1-6 hours, or 6-12 hours, or 12-18 hours, or 24 hours, or even 2 or 3 days. Typically, a minimum incubation time is the time needed for tissue sections to no longer float, i.e., when the tissue section has sunk to the bottom of the solution.

In some embodiments, the biological tissue is impregnated (incubated) with the optical clearing solution in successive steps in which the concentration of glycerol in the optical clearing solution in each step increases. The final incubation step may use glycerol in a concentration of precisely, at least, or above, for example, 70 wt %, 80 wt %, 90 wt %, or higher (e.g., 95 wt % or 100 wt %). For example, the successive incubation steps may include the following steps: a first impregnating step employing an optical clearing solution containing only 20-50 wt % formamide in water; an intermediate impregnating step employing an optical clearing solution containing 20-50 wt % formamide, 30-60 wt % glycerol, and water; and a final impregnating step employing an optical clearing solution containing only 20-40 wt % formamide and 60-80 wt % glycerol, wherein the glycerol content increases from the intermediate impregnating step to the final impregnating step. The foregoing protocol may also include one or more additional intermediate incubation steps (e.g., second, third, or fourth intermediate incubation steps) in which the one more additional intermediate incubation steps employ optical clearing solutions containing a successively higher glycerol content (i.e., the optical clearing solution employed in the second intermediate incubation step contains a higher glycerol content than the optical clearing solution employed in the first intermediate incubation step). A second intermediate incubation step may employ an optical clearing solution containing, for example, 20-50 wt % or 20-40 wt % formamide; 40-60 wt %, 40-70 wt %, or 40-80 wt % glycerol; and water, provided that the second intermediate incubation step employs a higher glycerol content than the first intermediate incubation step. A third intermediate step, if present, may also be selected from the foregoing exemplary ranges for the second intermediate incubation step, provided that the third intermediate incubation step employs a higher glycerol content than the second intermediate incubation step. An alternative second intermediate incubation step (or a third or fourth intermediate incubation step) may employ an optical clearing solution containing, for example, 20-40 wt %, 20-30 wt %, or 15-25 wt % formamide; 60-80 wt %, 60-90 wt %, 70-80 wt %, or 70-90 wt % glycerol; and water, provided that successive steps employ clearing solutions containing a higher glycerol content.

In some embodiments, before the biological tissue is incubated with the optical clearing solution, the biological tissue is pre-treated with a blood decolorizing pre-treatment solution (i.e., "decolorizing solution") before the biological tissue is contacted with the optical clearing solution. The decolorizing solution may be any such solution well known in the art. The decolorizing solution typically includes hydrogen peroxide (either alone or with one or more other components) in an aqueous solution. The decolorizing solution may or may not also include a catalase inhibitor to decrease the ability of catalase in the blood to convert the hydrogen peroxide to water and oxygen. Some examples of catalase inhibitors include ascorbic acid, EDTA, certain flavonoids (e.g., myricetin, epicatechin gallate, and epigallocatechin gallate), hydroxylamine, potassium cyanide, hydrogen sulfide, and combinations thereof.

Notably, the present invention further includes sodium azide ($NaN_3$) in the decolorizing solution. As discussed later in further detail in the present disclosure, the presence of sodium azide in the decolorizing solution substantially slows the production of oxygen, which in turn prevents the rapid accumulation of large oxygen bubbles that generally result in tearing of the biological specimen when using conventional peroxide-based decolorizing solutions. Thus, the presence of sodium azide in the decolorizing solution has herein surprisingly been found to preserve tissue integrity. For purposes of the present invention, the sodium azide is generally included in an amount of 0.05-.5 wt %. In particular embodiments, the decolorizing solution may be specially formulated to contain the following components: (i) 10-30 wt % DMSO; (ii) 0.05-1 wt % or 0.05-.5 wt % sodium azide; (iii) 0.5-3 wt % or 0.2-2 wt % hydrogen peroxide, and (iv) phosphate buffered saline (PBS) solution as remainder, wherein the wt % values given are by weight of PBS solution. Typically, the biological tissue is submerged in cooled decolorizing solution, e.g., at no more than or less than 10° C., 5° C., or 0° C. for at least 6, 12, 18, or 24 hours.

After the biological tissue has been rendered sufficiently optically transparent, the biological tissue is viewed by three-dimensional light microscopy and/or fluorescent light-based microscopy, as well known in the art. Typically, the three-dimensional light microscope is equipped with, inter alia, a computer-controlled light source, camera system, automatic Z motor, and image processing unit, as described in, for example, Y. S. Rhyu et al., Applied Microscopy, 46(2), 93-99, 2016, the contents of which are incorporated herein by reference. The biological tissue being viewed by three-dimensional light microscopy (and which was treated with the above described optical clearing solution) may be any biological tissue of interest. The biological tissue may be, for example, neuronal (e.g., brain) tissue, heart muscle tissue, internal organ tissue (e.g., heart, bladder, stomach, kidney, intestine, lung, liver, testes, or ovaries), cancerous tissue, connective tissue, epithelial tissue, muscle tissue, fat cells, bone tissue, and blood cells. In some embodiments, the biological tissue being imaged is a cross-section, which may be a thick cross-section, e.g., 0.1, 0.5, 1, or 2 mm thickness. In other embodiments, the biological tissue may be a whole organ, such as any of the organs mentioned above.

In another aspect, the present disclosure is directed to a method for reducing auto-fluorescence in biological tissue to render the biological tissue imagable with enhanced resolution in a fluorescence-based imaging technique. In the method, biological tissue is incubated with an auto-fluorescence quenching solution for sufficient time for the auto-fluorescence quenching solution to impregnate the biological tissue and make the biological tissue sufficiently reduced in auto-fluorescence to permit imaging of the biological tissue in a fluorescence-based imaging technique with enhanced resolution. The terms "sufficient time" and "sufficiently reduced in auto-fluorescence" are readily understood by one skilled in the art of fluorescence-based imaging techniques and as similarly defined above for tissue preparation for three-dimensional light microscopy. The auto-fluorescence quenching solution includes at least the following four components: (i) ammonium bicarbonate in a concentration of 1-100 mM, (ii) copper sulfate in a concentration of 20-500 µM, (iii) DMSO in a concentration of 5-20 wt % (or, e.g., 5-15 wt %, 5-10 wt %, 10-15 wt %, 10-20 wt %, or 15-20 wt %), and (iv) water as remainder (typically in an amount of at least 30, 40, or 50 wt % and up to 60, 70, 80, or 90 wt %). In some embodiments, the auto-fluorescence quenching solution contains only the foregoing four components. In other embodiments, the auto-fluorescence quenching solution includes one or more additional components, such as PBS or other solvent (e.g., methanol or ethanol). In some embodiments, non-aqueous solvents are excluded. In different embodiments, the ammonium bicarbonate is present in the auto-fluorescence quenching solution in an amount of, for example, 1, 2, 5, 10, 20, 30, 40, 50, 60, 70, 80, 90, or 100 mM, or an amount within a range bounded by any two of the foregoing values (e.g., 1-100 mM, 1-50 mM, 2-50 mM, 5-50 mM, 10-50 mM, 1-40 mM, 2-40 mM, 5-40 mM, or 10-40 mM). In different embodiments, the copper sulfate is present in the auto-fluorescence quenching solution in an amount of, for example, 20, 30, 40, 50, 60, 70, 80, 90, 100, 150, 200, 250, 300, 350, 400, 450, or 500 µM, or an amount within a range bounded by any two of the foregoing values (e.g., 20-500 µM, 100-500 µM, 150-500 µM, 100-400 µM, 150-400 µM, 100-300 µM, 150-300 µM, 100-250 µM, or 150-250 µM). The auto-fluorescence quenching solution typically has a pH of 7-8, or more precisely a pH of about 7.5 (e.g., 7.2-7.8). In some embodiments, prior to incubating the biological tissue with the auto-fluorescence quenching solution, the biological tissue is rinsed at least twice with ultrapure water to reduce the content of ionic species in the biological tissue. In some embodiments, before imaging the biological tissue with fluorescence microscopy, the biological tissue is treated with a decolorizing solution and/or optical clearing solution, as described above.

After the biological tissue has been rendered sufficiently optically transparent or reduced in auto-fluorescence, the biological tissue is viewed by a fluorescence-based imaging technique, as well known in the art. Fluorescence-based imaging techniques are well known in the art. The fluorescence-based imaging technique may be, for example, a fluorescent stain or immunofluorescence (IF) imaging technique. The imaging technique may also operate in an epifluorescence, confocal, super-resolution, two-photon, or light-sheet imaging modality. Typically, the fluorescence-based imaging microscope is equipped with, inter alia, an arc lamp or laser light source, excitation filter, beam splitter, emission filter, camera system, automatic Z motor, and image processing unit. Fluorescence-based imaging microscopes and methods of use are described in, for example, T. Bihonegn, Journal of Medicine, Physiology and Biophysics, 44, ISSN 2422-8427, 2016, and M. Renz, Cytometry Part A, 83A: 767-779, 2013, the contents of which are incorporated herein by reference. The biological tissue being viewed by fluorescence-based imaging microscopy (and which was first treated with the above described auto-fluorescence quenching solution) may be any biological tissue of interest, such as earlier described above. The biological tissue may be, for example, neuronal (e.g., brain) tissue, heart muscle tissue, internal organ tissue (e.g., heart, bladder, stomach, kidney, intestine, lung, liver, testes, or ovaries), cancerous tissue, connective tissue, epithelial tissue, muscle tissue, blood cells, fat cells, and bone tissue. In some embodiments, the biological tissue being imaged is a cross-section, which may be a thick cross-section, e.g., 0.1, 0.5, 1, or 2 mm. In other embodiments, the biological tissue may be a whole organ, such as any of the organs mentioned above.

Examples have been set forth below for the purpose of illustration and to describe the best mode of the invention at the present time. However, the scope of this invention is not to be in any way limited by the examples set forth herein.

EXAMPLES

Synthesis of an Optical Clearing Solution ("Atacama Clear")

The following solutions 1-6 were prepared using molecular grade formamide (e.g. Sigma #F7503, ≥99%) and glycerol (Avantor #5092, ≥99.5%), and with ultra-pure distilled water.
1) 30% Formamide in water
2) 30% Formamide, 10% glycerol, in water
3) 30% Formamide, 25% glycerol, in water
4) 30% Formamide, 50% glycerol, in water
5) 30% Formamide, 70% glycerol
6) 20% Formamide, 80% glycerol Using Atacama Clear for Clearing Biological Tissue For these studies, heart sections were used because muscle is the most difficult tissue to clear, due to its extensive fibrous cellular structure. Tissues were incubated in increasing grades of glycerol, starting with solution 1 and progressing to solution 6 of the Atacama Clear (AT-C) formulation. Time of incubation can be varied depending on how thick and tough the tissues are, and whether they are embryonic or adult. Smaller and less tough tissues, as well as embryonic tissues, require less incubation. A good gauge for determining whether the tissue can progress to the next solution is to make sure the tissue section is not floating and has sunken to the bottom of container. Also, care should be taken to remove as much solution as possible when changing to the next step, blotting the tissue when possible.

Protocol:
A) Incubate tissue sections in solution 1, rocking overnight at 37° C. Eppendorf tubes mounted on a rotisserie rocker works well.
B) Incubate tissue sections in solution 2-6, rocking at 37° C. for at least 1 hour each, and until tissue sink.
C) Optional, leave in fresh solution 6 overnight at 37° C. with rocking. The next day, change to fresh solution 6.
After the above steps were completed, tissues were observed to be optically cleared and ready to be imaged when fully impregnated with solution 6.

Figure 1B:
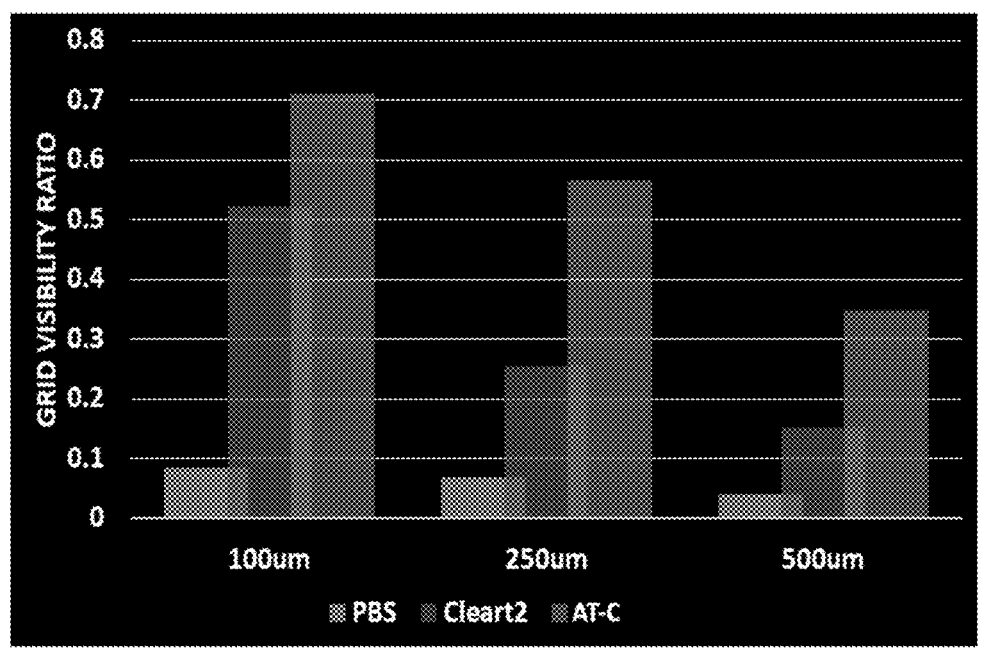

FIG. 1A shows a series of micrographs of tissue sections of varied thickness (i.e., 100, 250, and 500 µm), each treated with either PBS solution, ClearT$^2$ (conventional clearing solution containing 50% formamide and 20% PEG) (Kuwajima, T. et al., Development 140, 1364-1368, doi:10.1242/dev.091844, 2013), or Atacama Clear (AT-C). Surprisingly, as indicated in the micrographs, Atacama Clear optically clears tissues with approximately 50% more efficacy than ClearT$^2$. FIG. 1B is a graph plotting the quantified visibility (i.e., grid visibility ratio) of the grid paper below the tissue being imaged for tissue treated with PBS solution, ClearT$^2$, and Atacama Clear for the same 100, 250, and 500 µm thickness samples shown in FIG. 1A. As shown by the data in FIG. 1B, treatment with Atacama Clear resulted in substantially greater clearance compared to treatment with PBS or ClearT$^2$.

Decolorizing Pre-Treatment Using "Atacama-H$_2$O$_2$"

Preferably, before treating tissues with Atacama Clear, the tissues were pre-treated with a specially formulated decolorizing solution (i.e., Atacama-H$_2$O$_2$) containing hydrogen peroxide and sodium azide. Optical clearing is maximized by removal of blood, which impedes light penetration. Classical treatments have used hydrogen peroxide (H$_2$O$_2$) to decolorize and remove blood. These methods, however, cause a rapid and abundant accumulation of oxygen pockets throughout the sample as the blood-enzyme catalase converts H$_2$O$_2$ to water and oxygen, ultimately resulting in tissue tearing. To address this, a chemically controlled H$_2$O$_2$ treatment, termed "Atacama-H$_2$O$_2$", was herein developed. Atacama-H$_2$O$_2$ includes sodium azide, a moderate catalase inhibitor that decreases the reaction kinetics and precludes visible oxygenation. Consequently, Atacama-$H_2O_2$ decolorizes blood while preserving tissue integrity. Biological tissue is readily made optically transparent when Atacama-$H_2O_2$ is used prior to Atacama Clear.

The following stock solutions were used to make Atacama-$H_2O_2$: sodium azide solution, 5% (Fisher Bioreagent #71448-16), DMSO (Sigma #D8418, >99.9%), and hydrogen peroxide, 30% (Sigma Aldrich, #H1009). The final solution consisted of 20% DMSO, 0.1% sodium azide, and 1% $H_2O_2$ in PBS.

The following reagents were added in the following order (example given for 5 mLs):
Total 5 mLs
1. Add 3.80 mls of PBS
2. Add 1 ml of DMSO
3. Add 0.1 ml of 5% Sodium azide
4. Mix and let settle for 10 minutes
5. Add 0.166 ml of 30% $H_2O_2$
6. Chill on ice for 15 minutes The concentration of sodium azide can be modified to range from 0.05%-1% depending on whether the tissue is embryonic or adult, or the type of organ being studied. For an adult tissue that is heavily perfused with blood, such as the heart or kidney, a higher concentration of sodium azide can be used. Alternatively, embryonic tissues or adult tissue lacking much blood can be treated with lower levels of sodium azide.

After overnight treatment with Atacama-$H_2O_2$, the most prominent catalase activity subsided. At this point, if more blood clearing was required, the concentration of $H_2O_2$ in the solution was increased. For example, $H_2O_2$ can be increased to 2% and tissues further incubated at 4° C. The concentration of $H_2O_2$ can continue to be increased, as long as no visible oxygenation occurs.

Some tissues have extremely high blood content, such as freshly isolated and fixed hearts that have not been perfused with PBS or other solutions. For these tissues, a pretreatment may be needed before Atacama-$H_2O_2$ is used. A particularly effective pretreatment consists of a 5-10 minute incubation of tissue in ice-cold PBS solution containing 2.5% glacial acetic acid. This will eliminate excessive catalase activity, and blood clearing can then continue with Atacama-$H_2O_2$.

Using Atacama-$H_2O_2$

Tissues were submerged in ice-cold Atacama-$H_2O_2$, and then kept at 4° C. overnight with rocking. After overnight incubation, the extent of blood removal was gauged. If further treatment was needed, the sample was further incubated in Atacama-$H_2O_2$, or the concentration of $H_2O_2$ was progressively increased to 2-3%. The tissue, now rid of blood, was then treated with Atacama Clear.

Figure 2A:
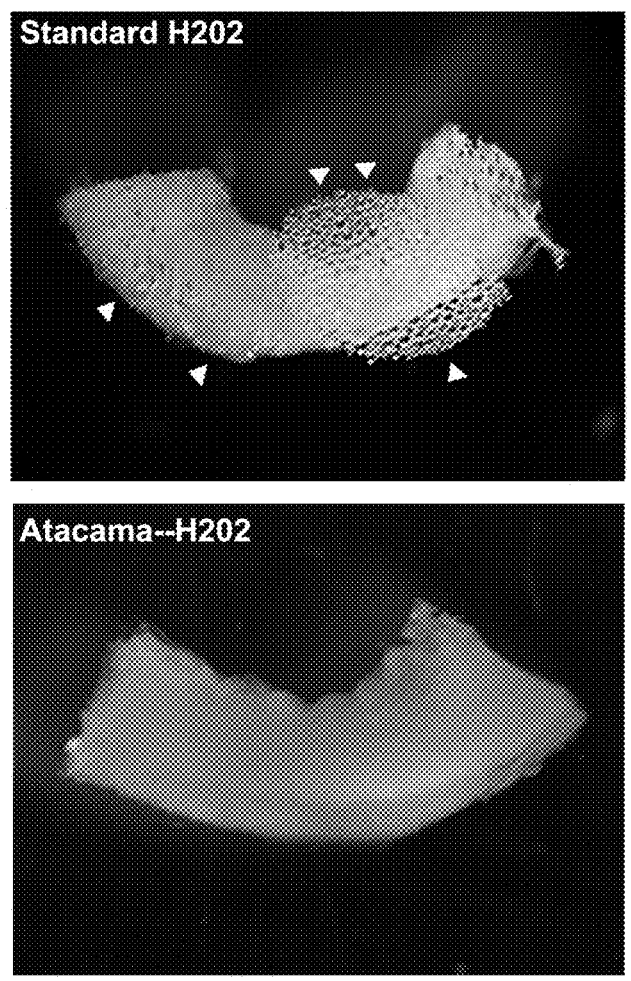
FIGS. 2A-2C.

FIG. 2A shows micrographs of heart muscle tissue treated with a standard peroxide decolorizing solution (top frame) and treated with Atacama-$H_2O_2$ (bottom frame). As shown in FIG. 2A (top), treatment of the tissue with standard peroxide decolorizing solution resulted in visibly fast and vigorous oxygen production. As shown in FIG. 2A (bottom), treatment of the tissue with Atacama-$H_2O_2$ resulted in a lack of visible oxygenation.

Figure 2B:
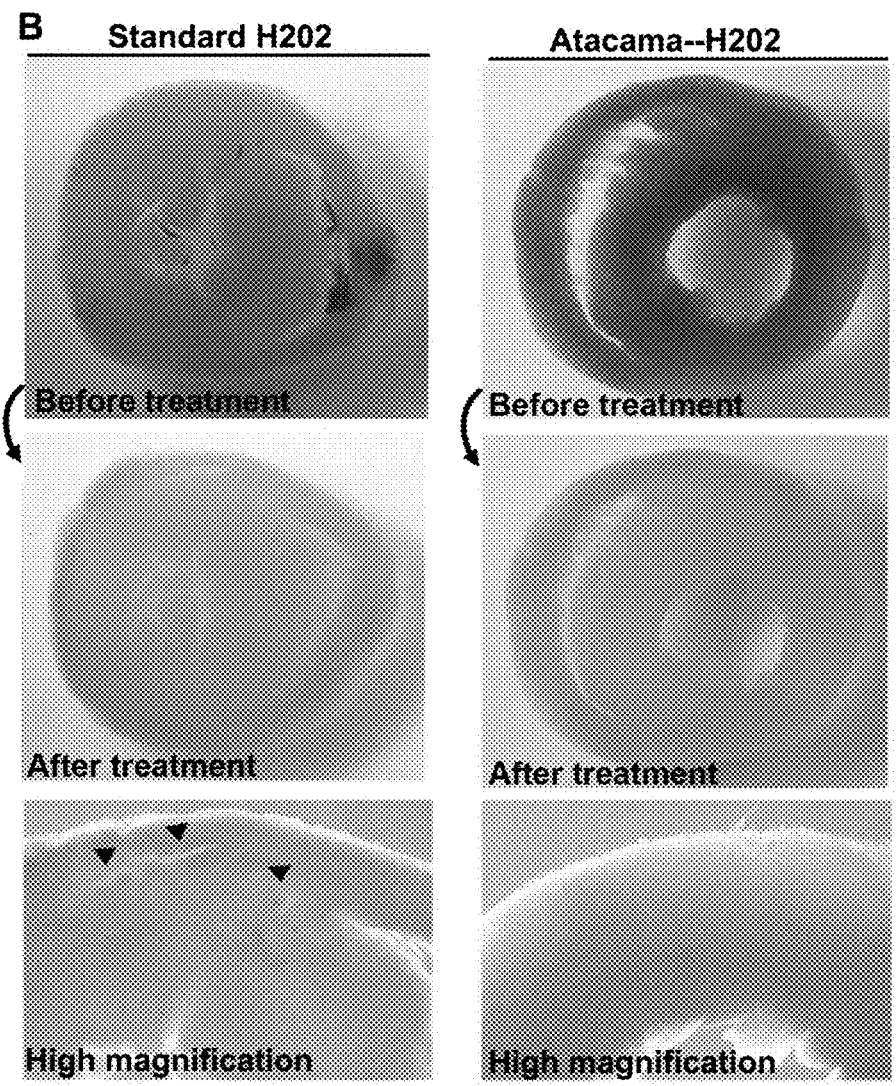

FIG. 2B shows micrographs of the heart muscle tissue treated with either standard peroxide decolorizing solution (left column) or Atacama-$H_2O_2$ (right column) Each of the left and right columns contains micrographs of the tissue before treatment (top frames), after treatment (middle frames), and at higher magnification after treatment (bottom frames). As shown by the micrographs in FIG. 2B, left column, particularly the high magnification (bottom) frame, treatment of the tissue with standard peroxide decolorizing solution resulted in visible tears in the tissue (see arrows). As shown by the micrographs in FIG. 2B, right column, particularly the high magnification (bottom) frame, treatment of the tissue with Atacama-$H_2O_2$ resulted in no observable tears in the tissue.

Figure 2C:
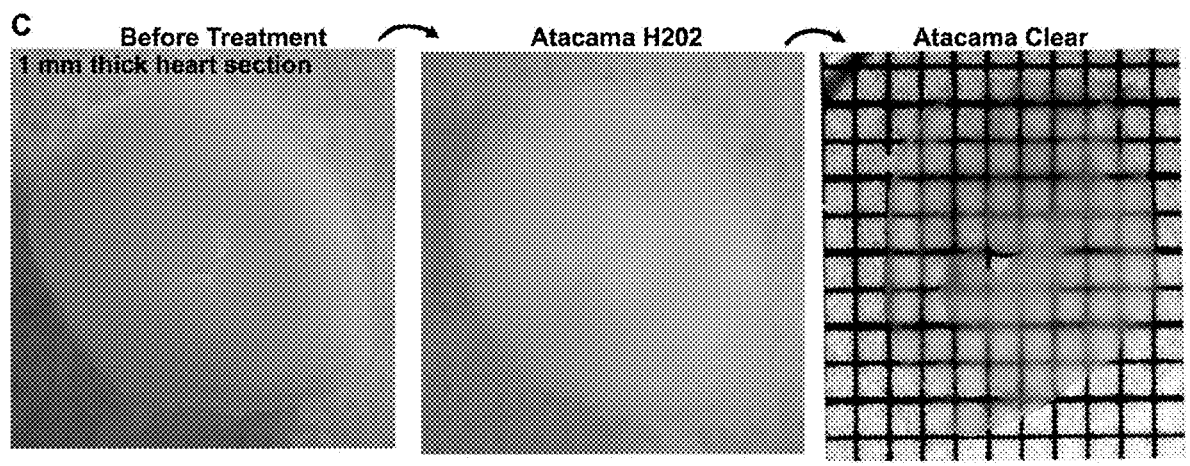

FIG. 2C shows micrographs of heart muscle tissue of 1 mm thickness (i) before any treatment (left frame), (ii) treated with Atacama-$H_2O_2$ (middle frame), and (iii) treated with Atacama-$H_2O_2$ prior to treatment with Atacama Clear (right frame). As shown, the use of Atacama-$H_2O_2$ in combination with Atacama Clear readily renders heart muscle tissue optically transparent.

Clearing of Whole Organs Using Atacama Clear

Figure 3:
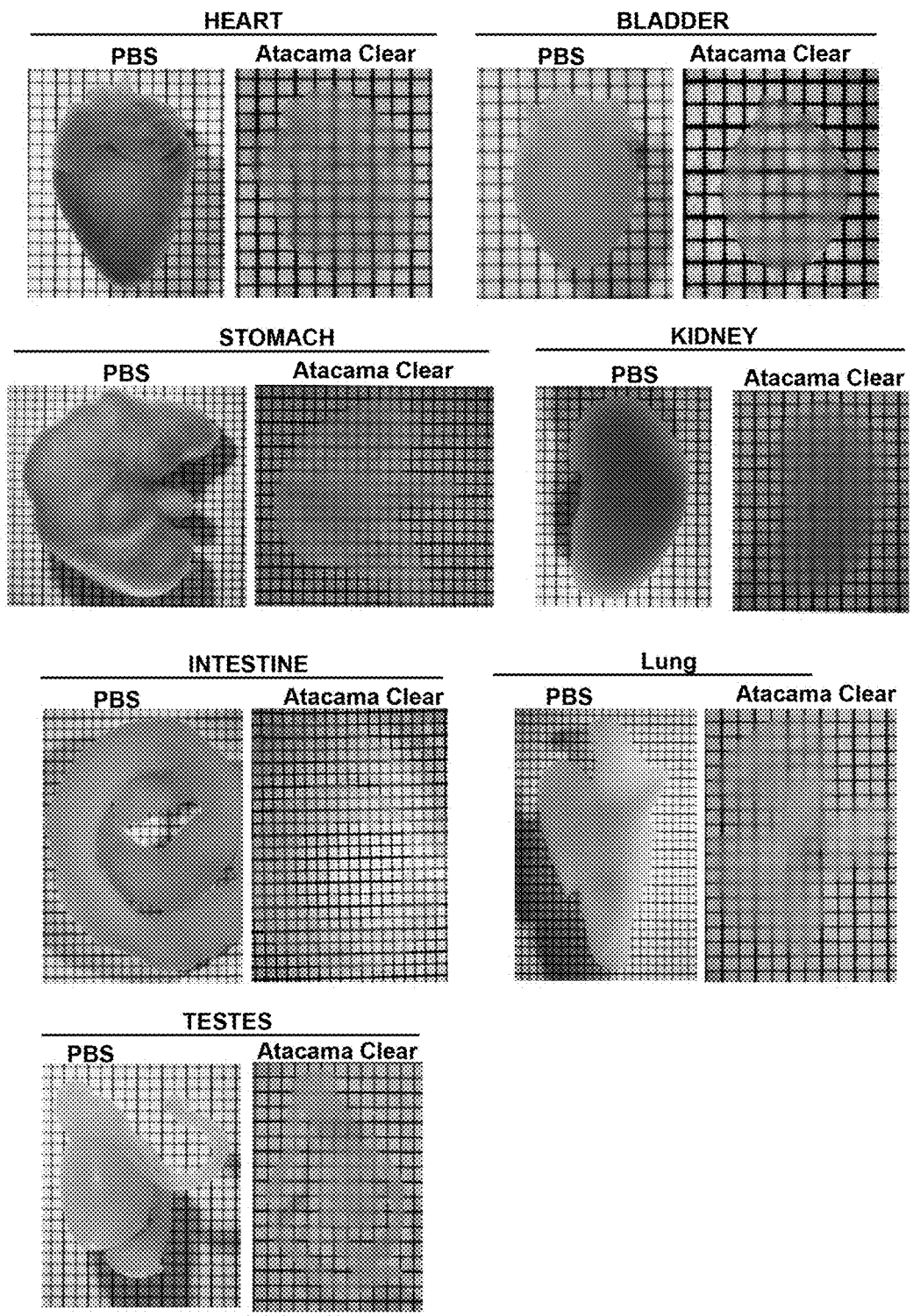
FIG. 3 shows the results of optically clearing of muscular organs, which are the most difficult to clear, including the heart, bladder, and intestine. Atacama-$H_2O_2$ pretreatment was used in combination with treatment with Atacama Clear to clear whole mouse organs. As shown in the micrographs in FIG. 3, mouse heart, bladder, stomach, kidney, intestine, lung, and testes were all successfully cleared.

Atacama-$H_2O_2$ pretreatment was used in combination with treatment with Atacama Clear to clear whole mouse organs. FIG. 3 shows the results of optically clearing of muscular organs, which are the most difficult to clear, including the heart, bladder, stomach, and intestine. As shown in the micrographs in FIG. 3, non-muscle intestinal organs were also readily cleared, including the kidney, lung and testes.

Figure 4A:
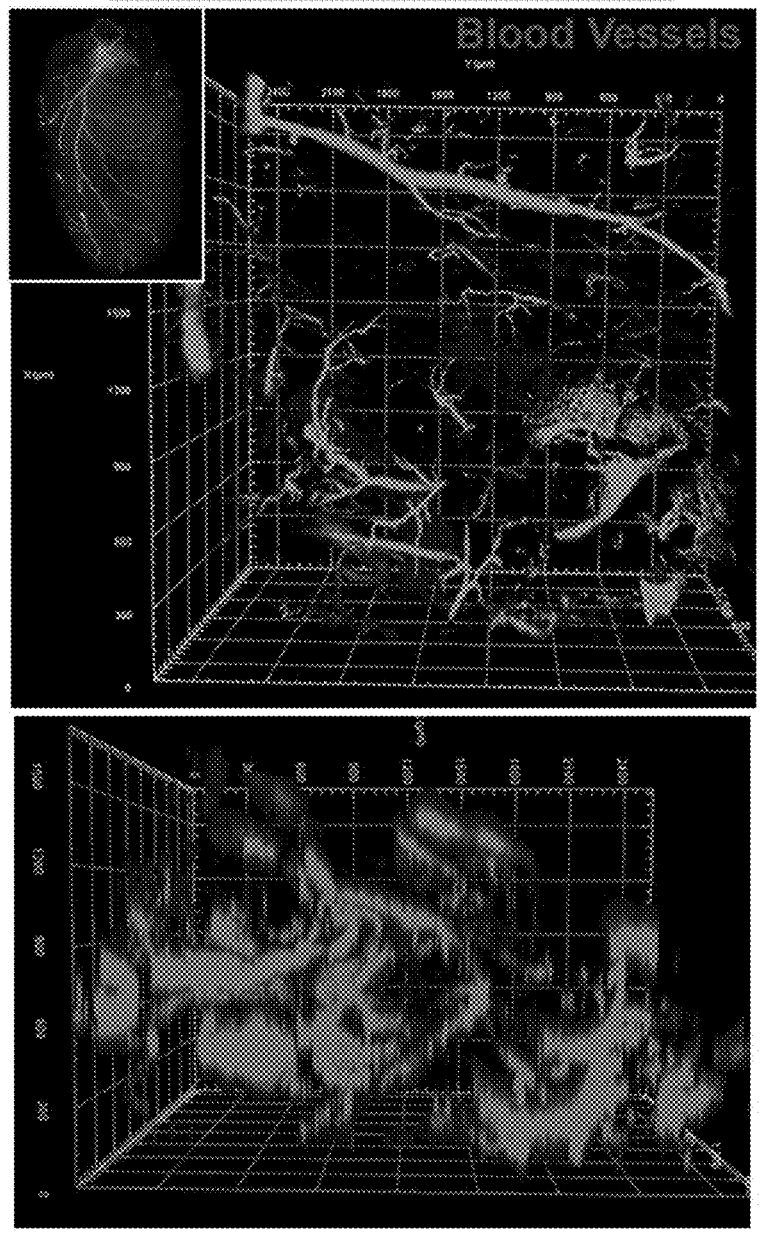
FIG. 4A demonstrates that Atacama Clear permits fluorescent light imaging deep within whole optically cleared hearts. In these studies, whole hearts were stained by IF for vascular smooth muscle actin (red) that labels the major cardiac arteries. The inset of the top micrograph panel shows a compound fluorescent light microscope image of the whole optically cleared stained heart. To demonstrate the capability of imaging deep within the tissue, confocal microscopy was used (top and bottom micrograph panels). Imaging was performed as deep as 1.8 mm into the heart muscle (bottom panel, Z axis orientation representative thickness depth of imaging).
Figure 4B:
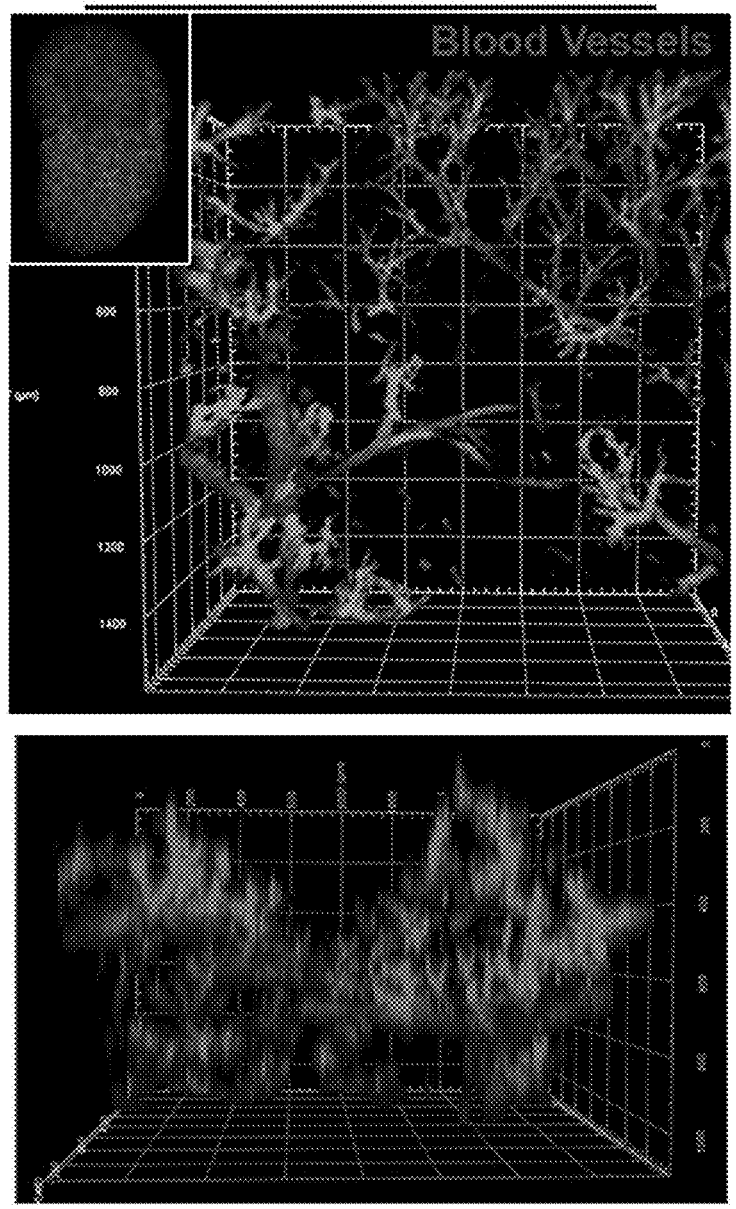
FIG. 4B demonstrates that Atacama Clear permits fluorescent light imaging deep within whole optically cleared kidneys. In these studies, whole kidneys were stained by IF for vascular smooth muscle acting (red) that labels the major renal arteries. The inset of the top micrograph panel shows a compound fluorescent light microscope image of the whole optically cleared stained kidney. To demonstrate the capability of imaging deep within the tissue, confocal microscopy was used (top and bottom micrograph panels). Imaging was performed as deep as 1.4 mm into the kidney (bottom panel, Z axis representative thickness depth of imaging).
Figure 4C:
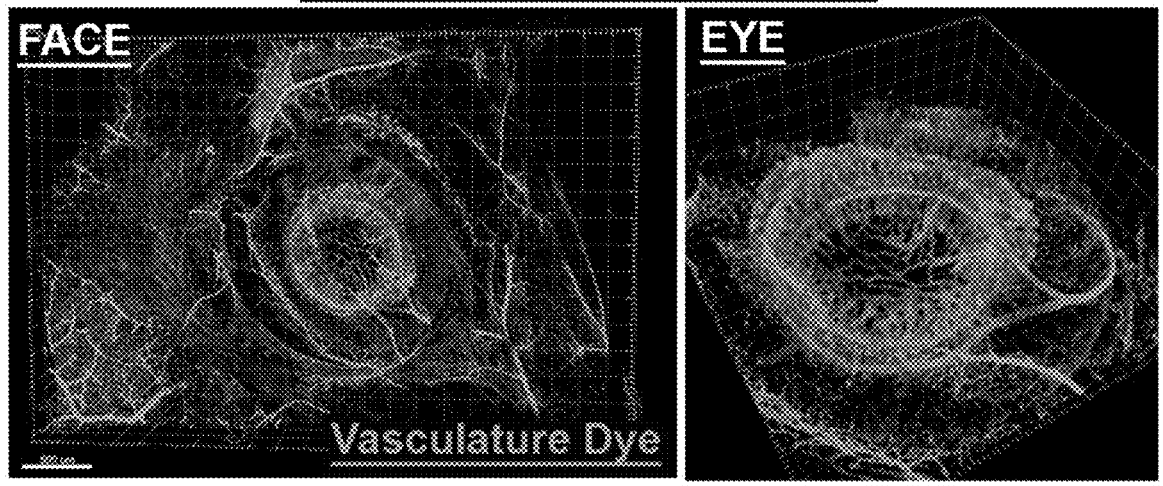
FIG. 4C demonstrates that Atacama Clear is compatible with fluorescinated lectin, an in vivo tracer that is used as an intravital dye injected into the circulation of animals and labels the vasculature that is conducting blood. Illustrated is the labeling of the blood conducting face vasculature (left panel), including the vasculature of the eye (right panel, high magnification of the eye).
Figure 4D:
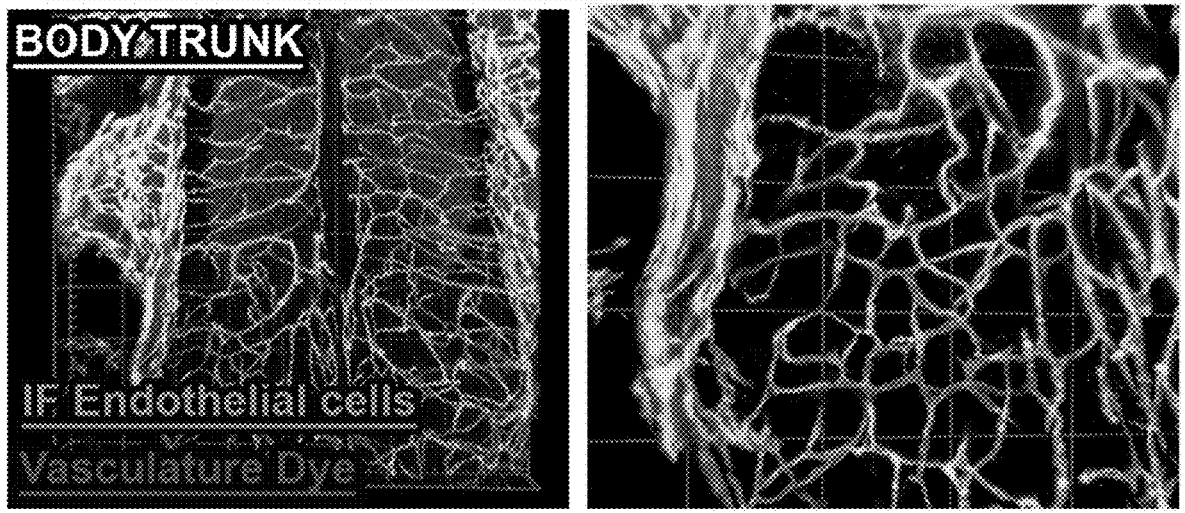
FIG. 4D demonstrates that Atacama Clear is compatible with studies using both fluorescinated lectin and traditional IF. Illustrated is lectin labeling of the blood conducting vessels (red) in the body of the embryonic mouse (embryonic Stg. 18.5), and IF labeling of the total vasculature (green). Notably, using Atacama Clear permits the visualization of mature vessels conducting blood (red) and immature vessels not yet conducting blood (green).
Figure 4E:
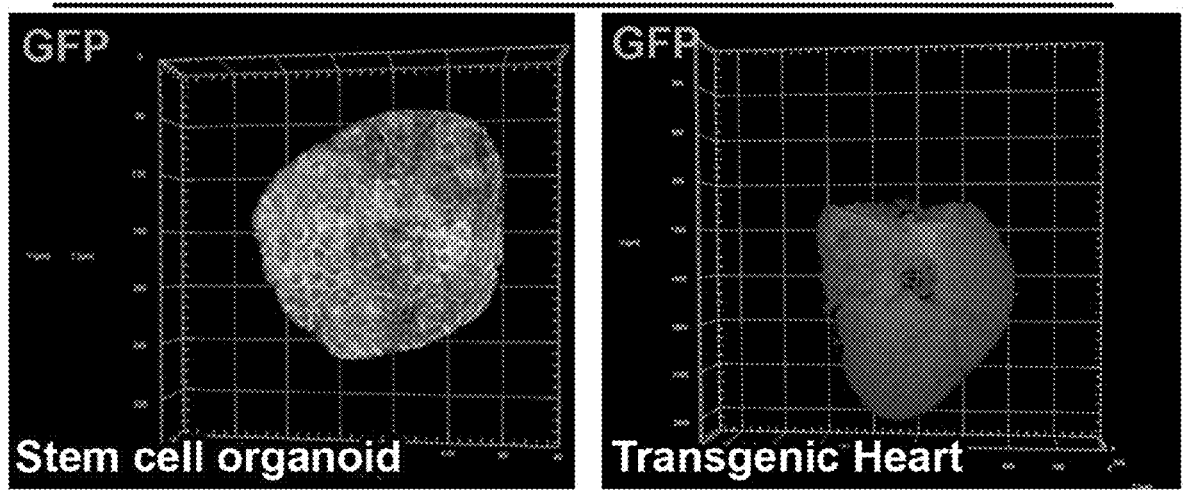
FIG. 4E demonstrates that Atacama Clear preserves the signal of fluorescent reporter proteins, a major limitation of currently used optical clearing solutions. The left panel shows GFP expression in an optically cleared stem cell organoid, which was also stained by IF for a ubiquitous cell membrane marker (red, cadherin staining). The right panel shows a transgenic zebrafish heart expressing GFP.
Figure 4F:
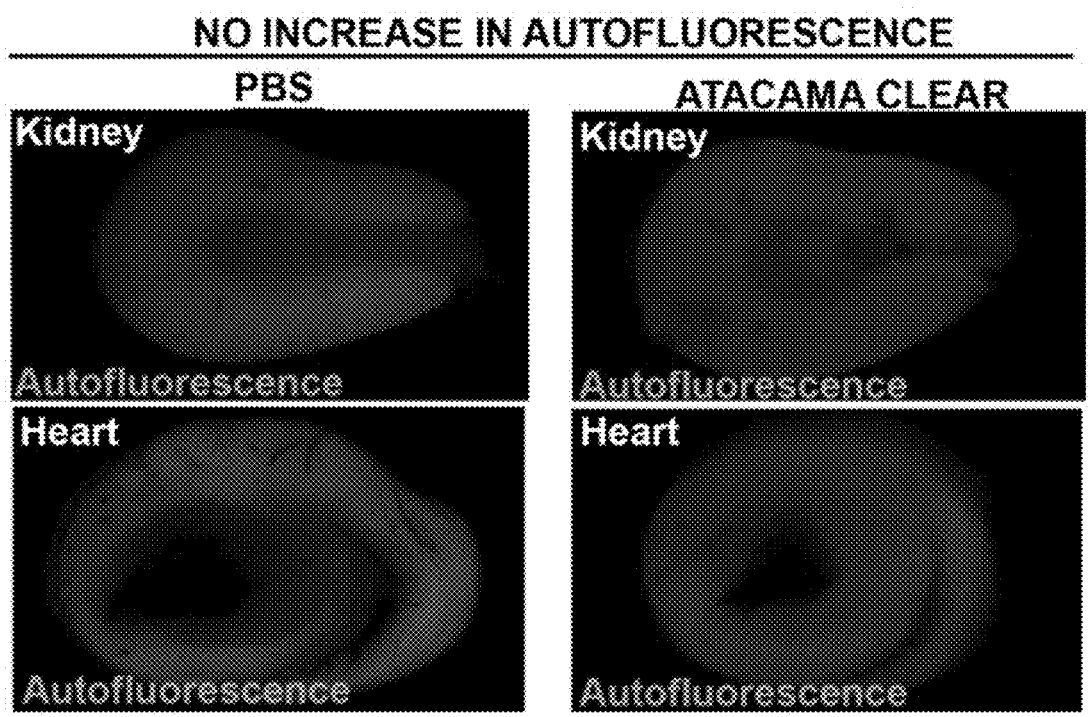
FIG. 4F demonstrates that Atacama Clear does not increase auto-fluorescence. Notably, currently used optical clearing solutions are know to increase auto-fluorescence, which makes imaging studies more limited. The left panels show the auto-fluorescence of the kidney and heart in PBS, and the right panels show the auto-fluorescence of the kidney and heart after using Atacama Clear.

FIGS. 4A-4F demonstrate the enhanced imaging properties provided by Atacama Clear. FIGS. 4A-4F demonstrate that Atacama Clear provides the following: 1) imaging of whole organs, including heart and kidney (FIGS. 4A and 4B); 2) use of intravital dyes, individually or in combination with immunofluorescence (FIGS. 4C and 4D); and 3) preserves the expression of fluorescent reporter proteins, including GFP (FIG. 4E); and 4) does not increase tissue auto-fluorescence (FIG. 4F). Notably, preservation of fluorescent reporter proteins is lacking in current 3D imaging techniques.

FIG. 4A shows that Atacama Clear permits visualization of optically cleared whole hearts assayed by IF (inset, whole heart image). In this example, whole hearts were stained with vascular smooth muscle actin (red) to label arteries. Confocal microscopy of the heart readily permitted the visualization of cardiac arteries (top panel). The bottom panel illustrates the Z axis orientation of confocal imaging that is representative of the thickness depth of imaging, which was 1.8 mm deep. Thus, Atacama Clear permits imaging deep within hearts.

FIG. 4B shows that Atacama Clear permits imaging of whole optically cleared kidneys assayed by IF (inset, whole kidney image). In this example, whole kidneys were stained with vascular smooth muscle actin to label arteries. Confocal microscopy of the kidney readily permitted visualization of the tree-like renal arterial bed (top panel). The bottom panel illustrates the Z axis orientation of confocal imaging that is representative of the thickness depth of imaging, which was 1.4 mm deep. Thus, Atacama Clear permits imaging deep within kidneys in IF studies FIG. 4C demonstrates that Atacama Clear is compatible with the in vivo tracer, fluorescinated lectin, which is injected into the circulation of animals and labels the vasculature that is conducting blood. Illustrated is the blood conducting vessels of the murine face (left panel), including a close up of the eye blood vessels (high magnification, right panel). Thus, lectin signal is preserved when optically clearing tissue with Atacama Clear.

FIG. 4D shows that Atacama Clear can be used in combinatorial studies using lectin and IF. Illustrated is the embryonic murine body trunk (Stg. 18.5) that has blood conducting vessels labeled with lectin (red) and the total vasculature labeled by IF (green). As can be seen in high magnification micrographs (right panel), combinatorial studies permit the visualization of mature blood vessels that conduct blood (yellow), as well as immature vessels that are not yet conducting blood (green). Thus, Atacama Clear is compatible with complex imaging studies incorporating tracers and IF.

FIG. 4E shows that Atacama Clear preserves the signal of fluorescent reporter proteins. The left panel shows a stem cell organoid that expresses GFP. For these studies, the organoid was stained for a ubiquitous cell membrane marker (cadherin, red) by IF. The organoid was then optically cleared with Atacama Clear, and imaged by confocal microscopy. As can be seen, GFP signal persists and are readily detected in combination with cadherin. The right panel of 4E shows a transgenic zebrafish heart expressing GFP. The GFP signal was also readily detectable in transgenic hearts. Thus, Atacama Clear permits the preservation of fluorescent reporter proteins, a major limitation of currently used optical clearing techniques.

FIG. 4F demonstrates that Atacama Clear does not increase tissue auto-fluorescence. The left panels show the green auto-fluorescence in untreated kidney and heart sections. The right panels show green auto-fluorescence in kidney and heart sections optically cleared with Atacama Clear. As can be seen, auto-fluorescence was not detectably increased. Notably, a major limitation of currently used optically clearing techniques is that they increase the auto-fluorescence of tissue. In this respect, current 3D imaging methods tend to substantially increase tissue auto-fluorescence.

Atacama Clear Permits Multi-Label Fluorescent Imaging Studies

The enhanced 3D imaging properties of Atacama Clear permits multi-label immunofluorescence of organs that are intrinsically difficult to image. For example, the kidney naturally exhibits high auto-fluorescence. Moreover, conventional 3D imaging techniques further increase auto-fluorescence. The resultant compounded auto-fluorescence precludes the ability to use fluorescent labels across the fluorescent light spectrum, e.g., green light auto-fluorescence is so high researchers often have to avoid imaging in this field.

Figure 5:
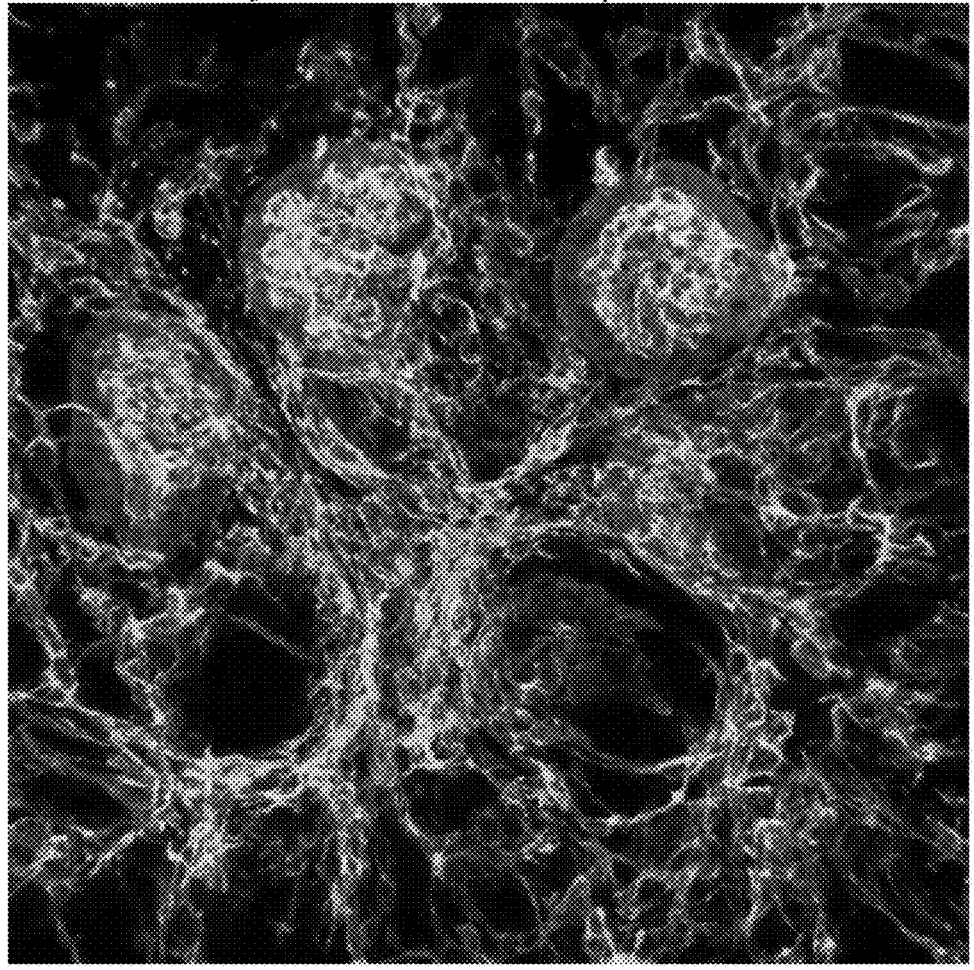
FIG. 5 is a micrograph demonstrating that Atacama Clear is compatible with multiple IF labeling studies. Three cell types were assayed in the kidney and were readily visualized and distinguished. As shown by FIG. 5, the enhanced capability of Atacama Clear permits imaging across the fluorescent spectrum, including blue, green, and red fluorescent signal.

The following experiment demonstrates the ability of Atacama Clear to enhance imaging in multi-label fluorescence. Embryonic day 15.5 kidneys were assayed by IF for podocalysin (red) to label podocytes, PDGFR-$\beta$ (blue) to label mesangial and vascular mural cells, and endomucin (green) to label the renal vasculature and glomerular capillaries. Kidneys were then optically cleared with Atacama Clear and imaged by confocal microscopy, with resultant image shown in FIG. 5. FIG. 5 demonstrates that Atacama Clear is compatible with multiple IF labeling. All three cell types assayed were readily visualized and distinguished. As shown by FIG. 5, the enhanced capabilities of Atacama Clear permits imaging across the fluorescent spectrum, including blue, green, and red fluorescent signal.

Reduction of Tissue Auto-Fluorescence Using "Atacama Quench"

As well known, tissue auto-fluorescence limits the usability of imaging intact tissues in 3D. To date, no optical clearing protocol has sufficiently addressed tissue auto-fluorescence. Notably, copper ions have been reported to have auto-fluorescent quenching properties, albeit at high concentrations (millimolar range) in the presence of acidic ammonium acetate (pH=5.0) that damages proteins and fluorophores used in IF (Schnell, S. A. et al., *J. Histochem Cytochem* 47, doi: 10.1177/002215549904700601, 1999; and Yang, J. et al., *Wellcome Open Research* 2, doi: 10.12688/wellcomeopenres.12251.1, 2017). Moreover, successful use of lower copper concentrations to reduce auto-fluorescence have not been reported. However, Atacama Quench, as developed herein, overcomes the above noted problems of the art by using a substantially lower concentration of copper but while maintaining exceptional auto-fluorescent quenching ability by virtue of a unique combination of additional components. Aside from copper metal ions in water, Atacama Quench contains ammonium bicarbonate along with dimethyl sulfoxide (DMSO) as a carrier. Surprisingly, Atacama Quench substantially eliminates tissue auto-fluorescence even with micromolar concentrations of copper ions. Atacama Quench also advantageously conserves tissue protein expression, and by consequence, dramatically increases the signal-to-noise ratio of IF studies. Atacama Quench is also non-toxic and completely compatible with Atacama-$H_2O_2$ and Atacama Clear formulations described above.

Making Atacama Quench

The following solutions should be made with molecular grade ammonium bicarbonate (e.g. Sigma #09830, >99.5%), copper(II) sulfate (Fluka #35185, 0.1M solution), DMSO (Sigma #D8418, >99.9%) and ultrapure distilled water ($DH_2O$).

The following components were added in a step-wise manner (example given for 10 mls), with vortexing of the solution as new reagent is added:
$DH_2O$=6.98 mls
DMSO=1 ml (10% final)
$NH_4HCO_3$ (100 mM stock, pH=7.45)=2 mls (20 mM final)
$CuSO_4$ (0.1 M stock solution)=0.020 mls (200 µM final)
Total volume=10 mls
Atacama Quench solution can be scaled up accordingly.

Atacama Quench is a simple ionic solution that does not rely on solvents to quench auto-fluorescence. Due to the simplicity of its chemical makeup, Atacama Quench can be susceptible to contaminating ions. Thus, in some embodiments, it is preferable that tissues be rinsed with $DH_2O$ several times before treating with Atacama Quench. Moreover, Atacama Quench is best made fresh from stock solutions directly before use.

Using Atacama Quench

A) Tissue to be treated was first rinsed with $DH_2O$ several times before use, e.g. 3×10 minute washes. Eppendorf tubes mounted on a rotisserie rocker work well.
B) Atacama Quench was prepared directly before use.
C) Atacama Quench was added to tissues and incubated at 37° C. overnight, preferably with rocking on a rotisserie shaker and container wrapped in aluminum foil to keep light out and conserve temperature.
D) Tissue was rinsed with $DH_2O$ several times, e.g. 3×10 minute washes.
E) Tissue was rinsed with PBS.

Using the above protocol, tissues were quenched of auto-fluorescence, and were ready for use in downstream fluorescent studies, such as IF. Notably, the extent of auto-fluorescence greatly varies among samples. To tailor the protocol for reducing auto-fluorescence, it is possible to adjust the concentration of $CuSO_4$, e.g. low concentrations of 20 µM for very little auto-fluorescence, to a high concentration of 500 µM or more in highly auto-fluorescent tissue. The duration of incubation may also be increased using Atacama Quench (e.g., using 200 µM $CuSO_4$) solution to continue quenching auto-fluorescence. For example, overnight incubation will generally provide significantly more AF quenching than one hour of incubation. Atacama Quench can be used to quench auto-fluorescence in any fluorescent-based technique, including IF, fluorescent RNA and DNA in situ hybridization, STORM super resolution imaging, and retrograde tracing of fluorescent probes.

Atacama Quench Substantially Eliminates Auto-Fluorescence (AF)

Figure 6A:
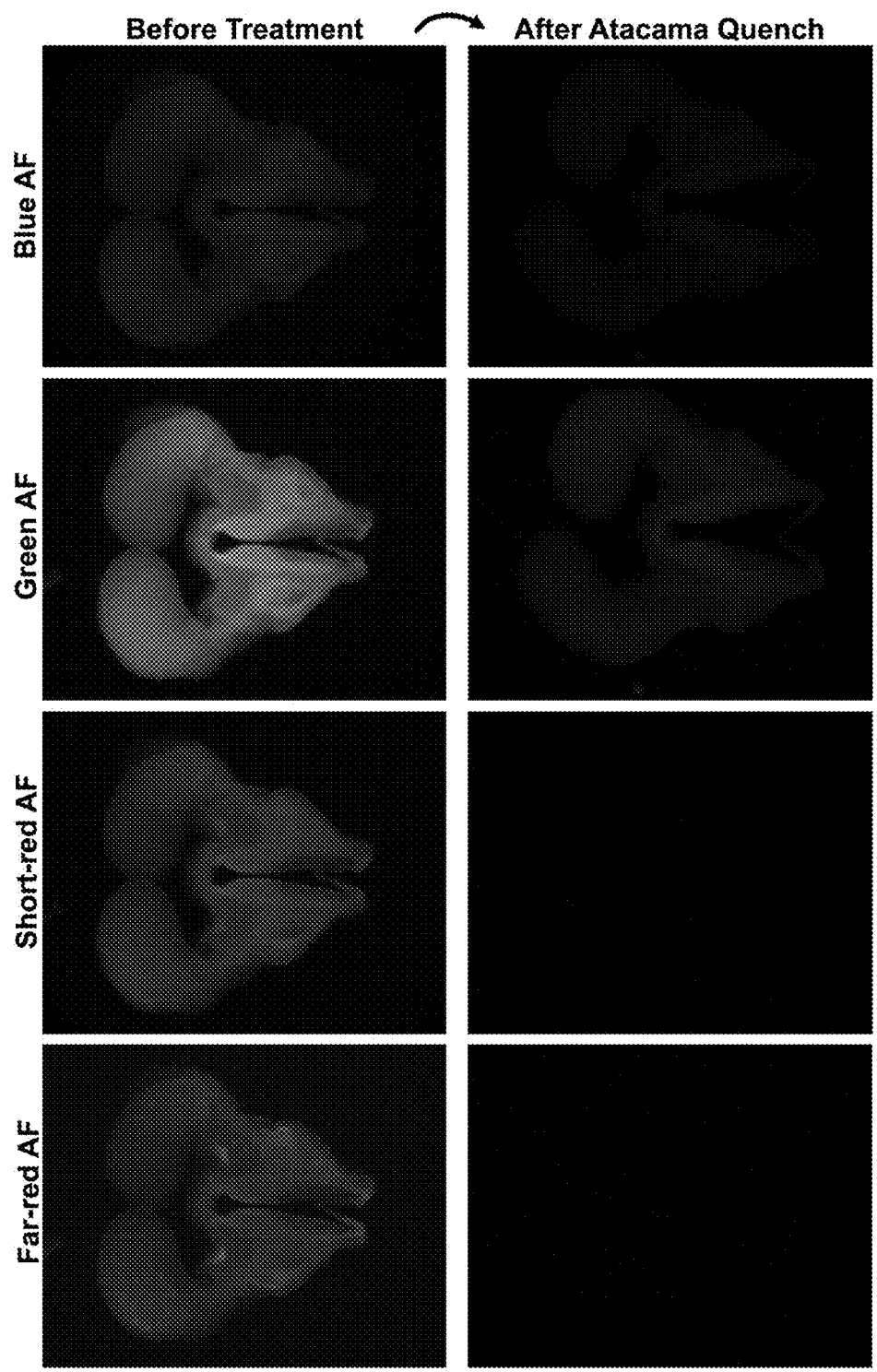
FIG. 6A shows the level of auto-fluorescence (AF) in murine brain tissues before treatment (left column) and after treatment with Atacama Quench (right column) for Blue AF, Green AF, Short-red AF, and Far-red AF.
Figure 6B:
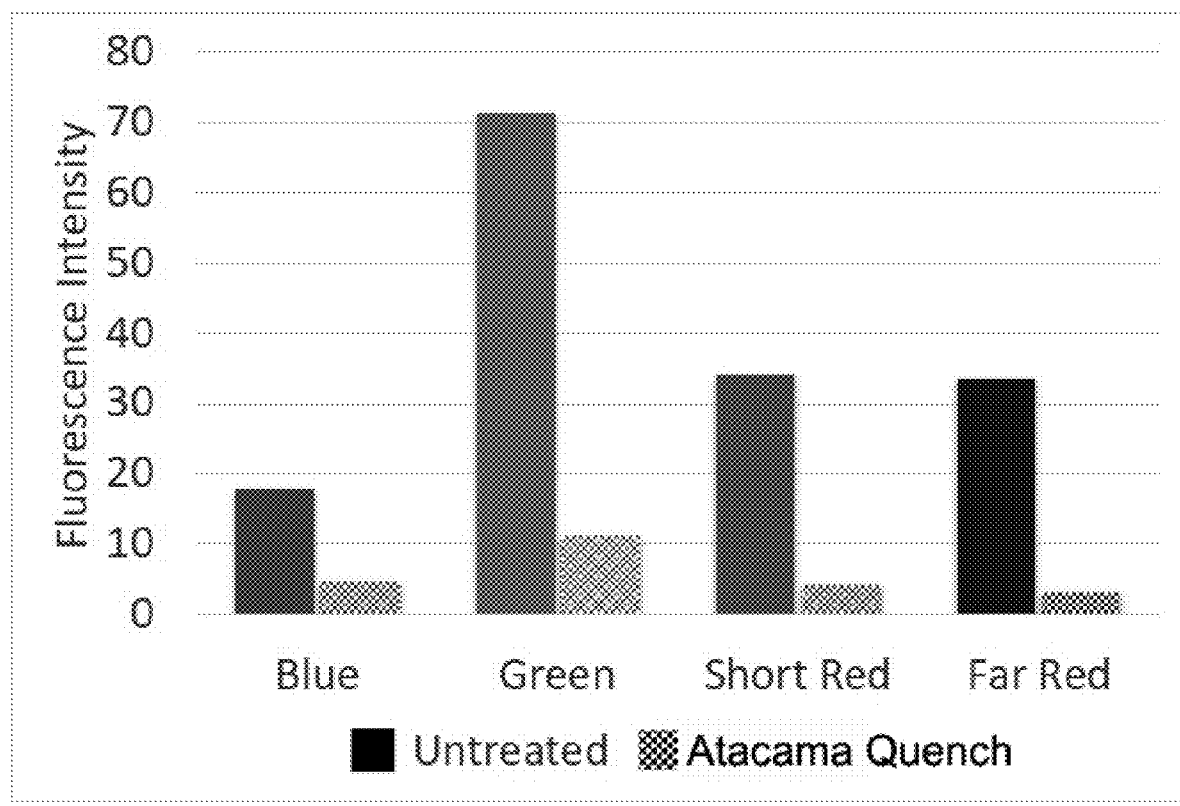
FIG. 6B is a graph plotting the auto-fluorescence levels measured in AF micrographs shown in FIG. 6A. As can be seen in 6B, Atacama Quench eliminates approximately 85% of green AF, the most prominent AF field, and almost completely eliminates short- and far-red AF.

FIG. 6 demonstrates that Atacama Quench eliminates auto-fluorescence across the fluorescent light spectrum. For these studies, embryonic day 10.5 murine brain tissues were treated with Atacama Quench to determine its efficacy in quenching tissues AF (FIG. 6A). Critically, brain tissues exhibit high tissue AF throughout the light spectrum, from blue-to-far red wavelengths (before treatment). Treatment with Atacama Quench vastly reduced AF across the light spectrum. FIG. 6A shows the level of auto-fluorescence in the murine brain tissues before treatment (left column) and after treatment with Atacama Quench (right column) for Blue AF, Green AF, Short-red AF, and Far-red AF. FIG. 6B is a graph plotting the auto-fluorescence levels measured in AF micrographs shown in FIG. 6A. As shown by the AF micrographs in FIG. 6A and resultant data in FIG. 6B, treatment with Atacama Quench resulted in up to 85% decrease in green auto-fluorescence (green AF) and nearly eliminated auto-fluorescence in the red light spectrum (short-red and far-red; see chart FIG. 6B).

Atacama Quench Increases the Signal-to-Noise Ratio in IF Imaging

Figure 7:
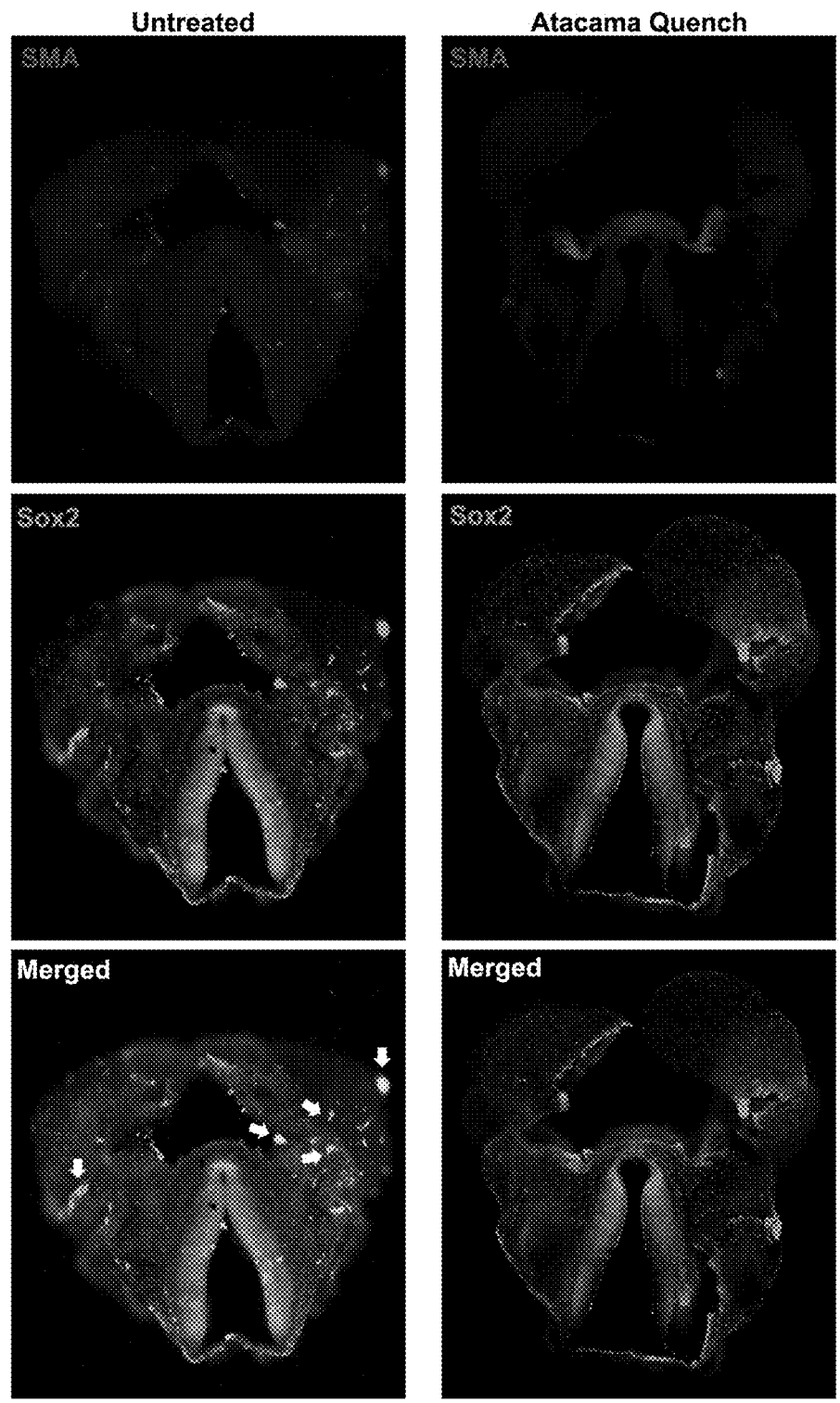
FIG. 7 shows that Atacama Quench increases the sensitivity of IF imaging studies. The micrographs are images of untreated murine brain tissue (in the left column) and images of murine brain tissues treated with Atacama Quench (in the right column) In both sample sets, the brain was stained for two distinct cell types, mural cells stained by smooth muscle actin (SMA) and neuronal cells stained by Sox2 (green). As can be seen in the untreated sample, there are areas of red/green co-expression (arrow, bottom left panel), which provides a false positive signal that these well established distinct cell types are of the same kind. By contrast, eliminating auto-fluorescence with Atacama Quench resulted in the differentiation between neuronal and mural cells (bottom right panel).

In this experiment, IF imaging was performed on brain tissues treated with and without Atacama Quench to determine if the decrease in AF conferred by Atacama Quench increases the sensitivity of IF studies. Specifically, E10.5 brains with and without Atacama Quench treatment were assayed by IF for two distinct cell lineages, vascular mural smooth muscle cells (SMA, red) and neural progenitor cells (Sox2, green). FIG. 7 shows the resulting IF imaging micrographs, with images of untreated tissue shown in the left column and images of tissue treated with Atacama Quench shown in the right column. The merged images represent the overlay of red and green micrographs, and sites of co-expression are denoted by yellow color in the merged images. Notably, in untreated tissues, auto-fluorescence resulted in a false positive signal of Sox2 and SMA co-expression (white arrows, merged untreated), despite these cell types coming from different cell progenitor lines. That is, in untreated samples, high AF resulted in positive overlap of neuronal (green, Sox2) and muscle (red, SMA) signals (arrows), despite these cell types being of distinct lineages. By contrast, treatment with Atacama Quench resulted in discrimination between smooth muscle and neural progenitor cell types. That is, Atacama Quench eliminated AF and readily permitted the differentiation between neuronal and vascular smooth muscle cells.

Figure 8:
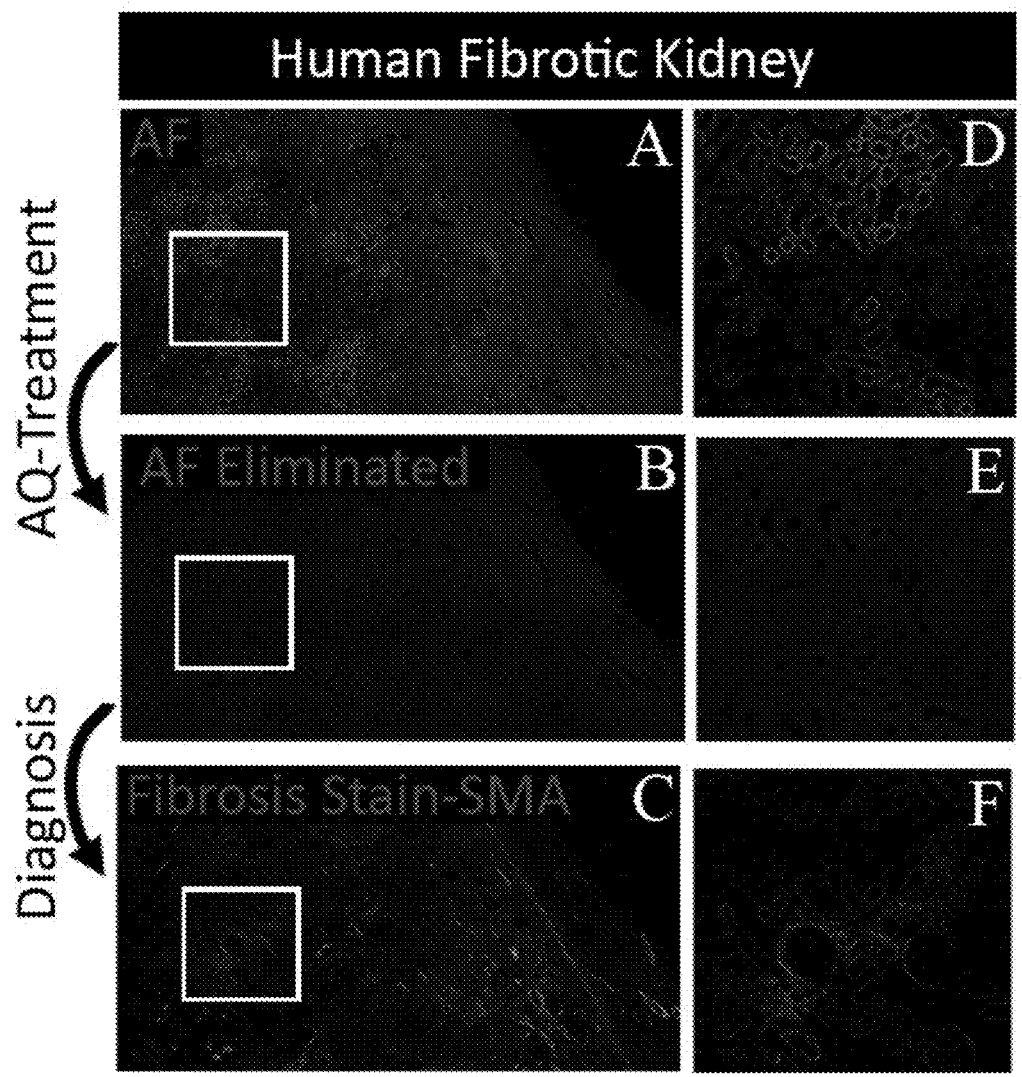
FIG. 8 shows a series of micrographs (labeled as panels A-F), wherein: panel A shows kidney tissue before AQ treatment (with boxed area enlarged in panel D), panel B shows kidney tissue after AQ treatment (with boxed area enlarged in panel E), and panel C shows kidney tissue after fibrosis staining (SMA, with boxed area enlarged in panel F). As this figure shows, diagnostic IF is greatly improved by eliminating auto-fluorescence, as the auto-fluorescent signal before quenching (D) is as strong as the fibrotic staining after quenching (F), illustrating that it would be difficult, if not impossible, to differentiate between these signals without quenching.

Atacama Quench Increases the Capability of Detecting Disease Markers in Human Biopsies Analyzed by Diagnostic Immunofluorescence Human biopsy samples have high auto-fluorescence, especially in organs, such as kidney tissue that exhibits acute auto-fluorescence. Moreover, human biopsies are commonly fixed with formaldehyde and then paraffin embedded (i.e., FFPE) for sectioning, which magnifies auto-fluorescence. Thus, FFPE kidney sections are among the most difficult tissue to assay for disease markers, which is a major limitation due to the large number of renal biopsies that are available for analysis. Thus, in another experiment, fibrotic FFPE kidney sections were assayed to determine if Atacama Quench (AQ) enhances the capability of detecting fibrosis. Specifically, human fibrotic kidneys were processed by FFPE, and then analyzed for the fibrotic marker smooth muscle actin (SMA). FIG. 8 shows a series of micrographs (labeled as panels A-F), wherein: panel A shows the kidney tissue before AQ treatment (with boxed area enlarged in panel D), panel B shows the kidney tissue after AQ treatment (with boxed area enlarged in panel E), and panel C shows the kidney tissue after fibrosis staining (SMA, with boxed are enlarged in panel F). Prior to treatment, the kidney biopsy exhibited a high level of AF (FIG. 8, panel A), and this AF was eliminated after treatment with AQ (FIG. 8, panel B). Once the AF of the kidney biopsy was eliminated, diagnostic analyses became straightforward, as can be seen by staining for the fibrotic marker smooth muscle actin (SMA, FIG. 8, panel C). Critically, high magnification views of the exact same region during each of the experimental steps (square white insets) show that the AF signal at the beginning (panel D) is just as strong as the signal for fibrosis (panel F), which demonstrates that it would be highly challenging and perhaps impossible to make a positive diagnosis without eliminating the AF. As can be observed from FIG. 8, Atacama Quench readily eliminates auto-fluorescence in the kidney, and permits the detection of fibrotic markers (SMA, red).

Atacama Quench (AQ) Eliminates Auto-Fluorescence in Human Brian Biopsies

Figure 9A:
FIGS. 9A-9B show that Atacama Quench is able to eliminate auto-fluorescence in human brain tissue, which is one of the most difficult tissues to perform IF staining because of its high auto-fluorescence.
Figure 9B:
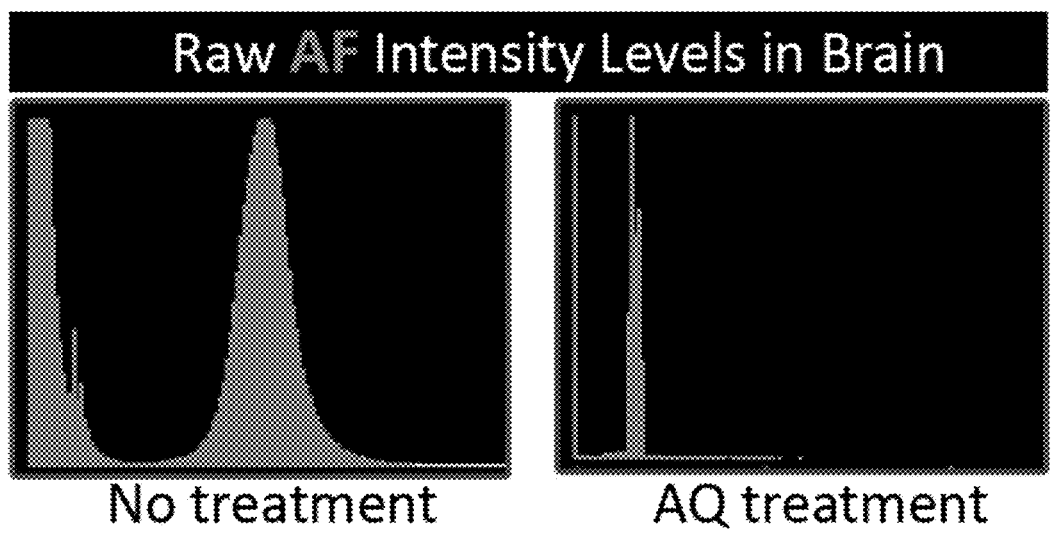

The human brain represents one of the most difficult tissues to image due to the extremely high level of auto-fluorescence it intrinsically exhibits. This limits the capability of performing diagnostic analyses of brain biopsies. Thus, as another experiment, human brain biopsies were assayed to determine if auto-fluorescence could be substantially reduced or eliminated by treatment with Atacama Quench. Surprisingly, these experiments show that auto-fluorescence can be reduced in human brain tissue by greater than 90% by treatment with Atacama Quench. FIG. 9A shows the level of AF in images of untreated (top) and AQ-treated (bottom) human brain tissue. As can be seen in FIG. 9A, the untreated brain tissue exhibits a high level of green AF, but this AF was nearly eliminated with AQ treatment. The level of AF observed in these tissues is quantified in graphs shown in FIG. 9B. Indeed, quantitation of raw fluorescent intensity levels for green AF shows that AQ eliminated greater than 90% AF in human brain samples.

Figure 10:
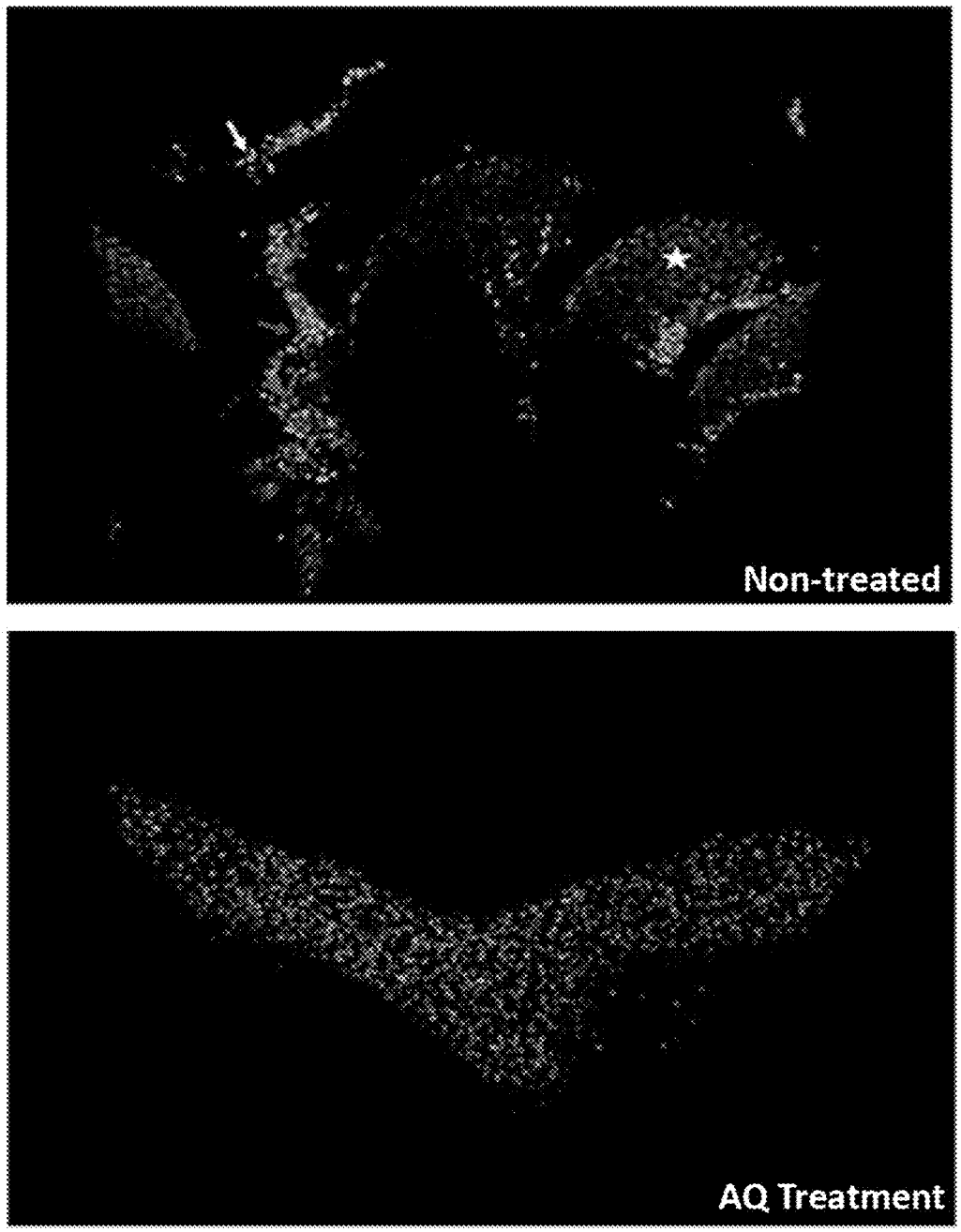
FIG. 10 shows that Atacama Quench does not eliminate fluorescent reporter protein expression.

Atacama Quench Eliminates Auto-Fluorescence without Quenching Endogenous Fluorescent Reporter Protein Expression Experiments were also conducted to determine whether Atacama Quench can eliminate auto-fluorescence while conserving endogenous fluorescent reporter protein expression. To this end, tissues from animals expressing Venus fluorescent protein in interstitial cells were untreated or treated with Atacama Quench and imaged, as shown in FIG. 10. In the non-treated tissue, Venus$^+$ cells could be detected (non-treated, top panel, white arrow), although background green fluorescence (non-treated, top panel, white star) made it difficult to distinguish Venus$^+$ cells from background in certain regions (non-treated, top panel, red arrow). By contrast, tissues treated with Atacama Quench exhibited a uniform Venus$^+$ signal, and lacked background auto-fluorescence (bottom panel).

While there have been shown and described what are at present considered the preferred embodiments of the invention, those skilled in the art may make various changes and modifications which remain within the scope of the invention defined by the appended claims.

What is claimed is:

1. A method for reducing auto-fluorescence in biological tissue to render the biological tissue imagable with enhanced resolution in a fluorescence-based imaging technique, the method comprising incubating biological tissue with an auto-fluorescence quenching solution for sufficient time for the auto-fluorescence quenching solution to impregnate the biological tissue and make the biological tissue sufficiently reduced in auto-fluorescence to permit imaging of the biological tissue in a fluorescence-based imaging technique with enhanced resolution, wherein said auto-fluorescence quenching solution comprises: (i) ammonium bicarbonate in a concentration of 1-100 mM, (ii) copper sulfate in a concentration of 20-500 M, (iii) 5-20 wt % dimethyl sulfoxide DMSO, and (iv) water as remainder.

2. The method of claim 1, further comprising performing a fluorescence-based imaging technique on the biological tissue that has been reduced in auto-fluorescence.

3. The method of claim 1, wherein said auto-fluorescence quenching solution consists only of components (i)-(iv).

4. The method of claim 1, wherein said auto-fluorescence clearing solution comprises (i) ammonium bicarbonate in a concentration of 5-50 mM, (ii) copper sulfate in a concentration of 100-250 μM, (iii) 5-20% DMSO, and (iv) water as remainder.

5. The method of claim 1, wherein said auto-fluorescence quenching solution has a pH of 7-8.

6. The method of claim 1, wherein said auto-fluorescence quenching solution has a pH of about 7.5.

7. The method of claim 1, further comprising rinsing the biological tissue at least twice with ultrapure water before impregnating the biological tissue with said auto-fluorescence quenching solution, wherein said rinsing is conducted for sufficient time to reduce the content of ionic species in the biological tissue.

8. The method of claim 1, wherein said biological tissue is internal organ tissue.

9. The method of claim 8, wherein said internal organ tissue is brain tissue.

10. The method of claim 1, wherein said fluorescence-based imaging technique is immunofluorescence.

* * * * *